(12) United States Patent
Okamura et al.

(10) Patent No.: US 6,987,197 B2
(45) Date of Patent: Jan. 17, 2006

(54) ORGANOZIRCONIUM COMPOSITE AND METHOD OF SYNTHESIZING THE SAME, RAW MATERIAL SOLUTION CONTAINING THE SAME, AND METHOD OF FORMING LEAD ZIRCONATE TITANATE THIN FILM

(75) Inventors: Shingo Okamura, Naka-gun (JP);
Hideyuki Hirakoso, Yokohama (JP);
Nobuyuki Soyama, Naka-gun (JP);
Katsumi Ogi, Naka-gun (JP);
Yoshinori Takayama, Naka-gun (JP)

(73) Assignee: Mitsubishi Materials Corporation, Tokyo (JP)

( * ) Notice: Subject to any disclaimer, the term of this patent is extended or adjusted under 35 U.S.C. 154(b) by 190 days.

(21) Appl. No.: 10/634,767

(22) Filed: Aug. 6, 2003

(65) Prior Publication Data

US 2004/0034245 A1    Feb. 19, 2004

(30) Foreign Application Priority Data

Aug. 8, 2002 (JP) ............................. 2002-230829
Aug. 8, 2002 (JP) ............................. 2002-230830
Nov. 25, 2002 (JP) ............................. 2002-340381

(51) Int. Cl.
*C23C 16/40* (2006.01)
*C07F 7/00* (2006.01)

(52) U.S. Cl. .................. 556/40; 106/1.25; 427/255.36; 427/255.37

(58) Field of Classification Search .................. 556/40; 106/1.25; 427/255.36, 255.37
See application file for complete search history.

(56) References Cited

U.S. PATENT DOCUMENTS 6,521,770 B2 * 2/2003 Hirakoso et al. ............. 556/40
6,547,863 B2 * 4/2003 Onozawa et al. .......... 106/1.25

FOREIGN PATENT DOCUMENTS

WO    WO98/51837    11/1998

OTHER PUBLICATIONS

Anthony C. Jones, et al., Journal of the European Ceramic Society, 19 (1999), 1413-1434.
Okuhara, et al., Preliminary Manuscript of 47$^{th}$ Annual Meeting of The Japan Society of Applied Physics (May, 2000), p. 540, with English translation.

* cited by examiner

*Primary Examiner*—Porfirio Nazario-Gonzalez
(74) *Attorney, Agent, or Firm*—Oblon, Spivak, McClelland, Maier & Neustadt, P.C.

(57) ABSTRACT

The organozirconium composite of the present invention has a decomposition temperature which is near the respective decomposition temperatures of an organolead compound and an organotitanium compound. The raw material solution can precisely control the composition of a PZT thin film over a broad temperature range. The raw material solution is less likely to react an organolead compound even when mixed with the organolead compound. The present invention provides a raw material solution which is less likely to cause vapor phase cracking. The organozirconium composite comprises one, or at least two kinds of zirconium chelate complexes containing, as a ligand, both of a first β diketone and a second β diketone having a structure different from that of the first β diketone, wherein, when at least two kinds of zirconium chelate complexes are contained, the coordination numbers of the first β diketone and the second β diketone that coordinate to at least two kinds of zirconium chelate complexes vary depending on the respective zirconium chelate complexes.

34 Claims, 10 Drawing Sheets

ORGANOZIRCONIUM COMPOSITE AND METHOD OF SYNTHESIZING THE SAME, RAW MATERIAL SOLUTION CONTAINING THE SAME, AND METHOD OF FORMING LEAD ZIRCONATE TITANATE THIN FILM

BACKGROUND OF THE INVENTION

1. Field of the Invention

The present invention relates to an organozirconium composite suitable for use as a raw material for formation of a complex oxide dielectric thin film used in a dielectric memory such as FeRAM (Ferroelectric Random Access Memory) or a dielectric filter using a Metal Organic Chemical Vapor Deposition method (hereinafter referred to as a MOCVD method), relates to a method of synthesizing the same, relates to a raw material solution containing the same, and relates to a method of forming a lead zirconate titanate thin film. More particularly, the present invention relates to an organozirconium composite suitable for formation of a lead zirconate titanate ($Pb(Zr,Ti)O_3$; PZT) thin film and a method of synthesizing the same, and a raw material solution containing the same.

2. Description of the Related Art

DRAM used mainly as a rewritable memory is a volatile memory and causes environmental problems because an electric current must be periodically applied to hold data in memory, and large amounts of power are consumed. Therefore, a ferroelectric memory such as FeRAM, which can store data in a non-volatile memory for a long time and consumes little power consumption and is also interchangeable with DRAM, has attracted special interest. Since the ferroelectric memory has various advantages such as low write voltage, high-speed writing, large number of writing, bit writing and random access, in addition to the above-described features, much research has been performed.

The ferroelectric memory is made of a ferroelectric thin film, as storage capacitors of DRAM, which is provided with a memory function by utilizing a polarization hysteresis phenomenon of the ferroelectric thin film ferroelectric thin film. As the ferroelectric thin film, complex oxide materials having large spontaneous polarization such as PZT are used.

As an organozirconium compound used to form a PZT dielectric thin film, there is known a tetrakis-2,2,6,6-tetramethyl-3,5-heptanedionate zirconium (hereinafter referred to as $Zr(thd)_4$) complex in which a 2,2,6,6-tetramethyl-3,5-heptanedione residue (hereinafter referred to as thd) coordinates to zirconium. As an organolead compound, a bis-2,2,6,6-tetramethyl-3,5-heptanedionate lead (hereinafter referred to as $Pb(thd)_2$) is known. As an organotitanium compound, diisopropoxybis-2,2,6,6-tetramethyl-3,5-heptanedionate titanium (hereinafter referred to as $Ti(iPrO)_2(thd)_2$) is known.

It is reported that a film forming temperature of the $Zr(thd)_4$ complex among these complexes shifts from film forming temperatures of other organolead and organotitanium compounds when a PZT dielectric thin film is formed because the decomposition temperature is higher than the decomposition temperatures of the $Pb(thd)_2$ complex and the $Ti(iPrO)_2(thd)_2$ complex (see, for example, Anthony C. Jones et al., Journal of the European Ceramic Society, 19 (1999), 1413–1434 (Document 1)).

Therefore, it is also proposed to use a tetratertiary-butoxy zirconium (hereinafter referred to as $Zr(tBuO)_4$) complex having a decomposition temperature lower than that of the $Zr(thd)_4$ complex as a raw material of a PZT thin film. However, it is very difficult to handle the compound disclosed in the above-mentioned document because it is highly reactive with air.

As a novel organozirconium compound for MOCVD to solve the above-described problems, a diisopropoxybis-2,2,6,6-tetramethyl-3,5-heptanedionate zirconium (hereinafter referred to as $Zr(iPrO)_2(thd)_2$) complex, a ditertiary-butoxybis-2,2,6,6-tetramethyl-3,5-heptanedionate zirconium (hereinafter referred to as $Zr(tBuO)_2(thd)_2$) complex and a $Zr_2(iPrO)_6(thd)_2$ complex are disclosed (see, for example, PCT International Publication Number WO98/51837 (Document 2)). These novel organozirconium compounds are superior to the above-described conventional organozirconium compounds because a film can be formed over a broad temperature range.

As another novel organozirconium compound for MOCVD, an isopropoxytris 2,2,6,6-tetramethyl-3,5-heptanediolnate zirconium (hereinafter referred to as $Zr(iPrO)(thd)_3$) complex is proposed (see, for example, OKUHARA et al., Preliminary Manuscript of 47th Annual Meeting of The Japan Society of Applied Physics (May, 2000), p540 (Document 3)). The proposed organozirconium compound is a monomer and has properties such as high vapor pressure and high solubility in solvent.

However, the organozirconium compound disclosed in Document 2 had the following drawbacks. That is, when mixed with an organolead compound to form a PZT dielectric thin film by the MOCVD method, the organozirconium compound is liable to react with the organolead compound and is not sufficiently vaporized when vaporized and introduced into a film forming chamber, and thus almost all of the compound is left as a residue.

The organozirconium compound disclosed in Document 3 has the following problems. That is, the compound per se is liable to leave a large amount of a vaporization residue and, furthermore, the compound is not sufficient vaporized upon introduction into a film forming chamber after vaporization, and therefore a large amount of the compound is left as a residue.

As a zirconium material for solving the above-described problems, the present inventors tentatively used a $Zr(tBuO)(thd)_3$ complex and a $Zr(tAmO)(thd)_3$ complex. However, these zirconium materials cause a disproportionate reaction to form $Zr(thd)_4$ over time in the case of dissolving in an organic solvent to obtain a raw material solution.

Also a study on a compound having a low decomposition temperature has been made and the subject of the study is tetrakis-2,6-dimethyl-3,5-heptanedionate zirconium (hereinafter referred to as $Zr(dhd)_4$) in which a 2,6-dimethyl-3,5-heptanedione residue (hereinafter referred to as dhd) coordinates to zirconium. However, $Zr(dhd)_4$ has a low decomposition temperature compared to an organotitanium compound such as $Ti(iPrO)_2(thd)_2$ and has a problem in that it is difficult to control the film composition.

SUMMARY OF THE INVENTION

A first object of the present invention is to provide an organozirconium composite having a decomposition temperature which is near the respective decomposition temperatures of an organolead compound and an organotitanium compound, and a method of synthesizing the same.

A second object of the present invention is to provide a raw material solution containing an organotitanium composite, which can precisely control the composition of a PZT thin film over a broad temperature range.

A third object of the present invention is to provide a raw material solution containing an organotitanium composite, which is less likely to react an organolead compound when mixed with the organolead compound.

A fourth object of the present invention is to provide a raw material solution containing an organotitanium composite, which is less likely to cause vapor phase cracking.

The present invention provides an organozirconium composite including one, or at least two kinds of zirconium chelate complexes containing, as a ligand, both of a first β diketone and a second β diketone having a structure different from that of the first β diketone, wherein, when the organozirconium composite includes at least two kinds of zirconium chelate complexes, the coordination numbers of the first β diketone and the second β diketone that coordinate to at least two kinds of zirconium chelate complexes vary depending on the respective zirconium chelate complexes.

In the present invention, the organozirconium composite including one or more kinds of zirconium chelate complexes containing both a first β diketone and a second β diketone as a ligand has a decomposition temperature which is near the respective decomposition temperatures of an organolead compound and an organotitanium compound compared to a conventional organozirconium composite. Therefore, when a film is formed by the MOCVD method using an organozirconium composite containing at least this complex as a raw material, the composition of a PZT thin film can be more precisely controlled over a broad temperature range. Since the organozirconium composite, which contains at least two kinds of zirconium chelate complexes in which the coordination number of the first β diketone and the coordination number of the second β diketone vary depending on the respective zirconium chelate complexes, has a decomposition temperature which is near the respective decomposition temperatures of an organolead compound and an organotitanium compound, the composition of a PZT thin film can be more precisely controlled over a broad temperature range.

The organozirconium composite of the present invention may further contain at least one of a first β diketone ligand and a second β diketone ligand.

The organozirconium composite of the present invention may further contain at least one of a zirconium chelate complex containing only the first β diketone as a ligand and a zirconium chelate complex containing only the second β diketone as a ligand.

In the organozirconium composite of the present invention, the first β diketone and the second β diketone are compounds selected from the group consisting of thd, dhd, acetylacetone residue (hereinafter referred to as acac), hexafluoroacetylacetone residue (hereinafter referred to as hfac), trifluoroacetylacetone residue (hereinafter referred to as tfac), trimethyloctanedione residue (hereinafter referred to as tod) and diphenylpropanedione residue (hereinafter referred to as dppd).

In the organozirconium composite of the present invention, the zirconium chelate complex may be obtained by reacting at least two kinds of β diketone compounds with a zirconium compound.

The zirconium chelate complex obtained by reacting at least two kinds of β diketone compounds with a zirconium compound can have a decomposition temperature which is near the respective decomposition temperatures of an organolead compound and an organotitanium compound because the decomposition temperature can be easily controlled compared to a conventional organozirconium composite. Therefore, when a film is formed by the MOCVD method using an organozirconium composite containing at least this complex as a raw material, the composition of a PZT thin film can be more precisely controlled over a broad temperature range.

In the organozirconium composite of the present invention, the zirconium chelate complex is a complex obtained by reacting at least two kinds of β diketone compounds with a zirconium compound, and its characteristic feature is that a mixing ratio of two kinds of β diketone compounds, that is, a mixing ratio of one β diketone compound A with the other β diketone compound B, (A/B), is from 80/20 to 20/80 in terms of molar ratio.

In the organozirconium composite of the present invention, at least two kinds of β diketone compounds are compounds selected from the group consisting of 2,6-dimethyl-3,5-heptanedione (hereinafter referred to as Hdhd), 2,2,6,6-tetramethyl-3,5-heptanedione(hereinafter referred to as Hthd), acetylacetone (hereinafter referred to as Hacac), hexafluoroacetylacetone (hereinafter referred to as Hhfac), trifluoroacetylacetone (hereinafter referred to as Htfac), trimethyloctanedione (hereinafter referred to as Htod) and diphenylpropanedione (hereinafter referred to as Hdppd).

In the organozirconium composite of the present invention, one β diketone compound may be Hdhd and the other β diketone compound may be Hthd.

The present invention provides a method of synthesizing an organozirconium composite, which comprises mixing a first β diketone compound with a zirconium chelate complex containing, as a ligand, a second β diketone having a structure different from that of the first β diketone compound.

According to the present invention, by mixing with the zirconium chelate complex containing the first β diketone and the second β diketone as a ligand, it is made possible to obtain an organopzirconium composite containing at least two kinds of zirconium chelate complexes in which the coordination number of the first β diketone and the coordination number of the second β diketone vary depending on the respective complexes.

In the synthesis method of the present invention, the amount of the first β diketone compound may be within a range from 100 to 1600 mol % based on the zirconium chelate complex containing the second β diketone as a ligand.

In the synthesis method of the present invention, the first β diketone compound may be Hthd and the zirconium chelate complex containing the second β diketone as a ligand may be $Zr(dhd)_4$.

In the synthesis method of the present invention, the first β diketone compound may be Hdhd and the zirconium chelate complex containing the second β diketone as a ligand may be $Zr(thd)_4$.

The present invention provides a method of synthesizing an organozirconium composite, which comprises dissolving a zirconium compound selected from zirconium butoxide, zirconium chloride and zirconium chloride oxide in an organic solvent, adding a mixed solution containing at least two kinds of β diketone compounds to the resulting solution, and heating the mixed solution under reflux at a temperature higher than a boiling point of the organic solvent contained in the mixed solution.

The synthesis method of the present invention is an improvement in the method of synthesizing an organozirconium composite by reacting two kinds of β diketone compounds with a zirconium compound, and a mixing ratio of two kinds of β diketone compounds, that is, a mixing ratio of one β diketone compound A with the other β diketone compound B, (A/B), may be from 80/20 to 20/80 in terms of molar ratio.

In the synthesis method of the present invention, at least two kinds of β diketone compounds may be compounds selected from the group consisting of Hdhd, Hthd, Hacac, Hhfac, Htfac, Htod and Hdppd.

In the synthesis method of the present invention, one β diketone compound may be Hdhd and the other β diketone compound may be Hthd.

Also the present invention provides a raw material solution including an organic solvent and an organozirconium composite of the present invention or an organozirconium composite obtained by the synthesis method of the present invention dissolved in the organic solvent.

The raw material solution obtained by dissolving an organozirconium composite in an organic solvent of the present invention can more precisely control the composition of a PZT thin film over a broad temperature range.

Also the present invention provides a raw material solution containing an organozirconium composite, including an organic solvent, and a first zirconium chelate complex in which a single kind of a β diketone compound coordinates to a center metal and a second zirconium chelate complex in which a single kind of a β diketone compound different from the β diketone compound coordinates to a center metal, which are dissolved in an organic solvent.

The raw material solution of the present invention can stably feed a material into a MOCVD apparatus because an increase in amount of a vaporization residue can be suppressed even when mixed with an organolead compound such as Pb(thd)$_2$. Furthermore, since the raw material solution thus prepared can be controlled to arbitrary vaporization and decomposition temperatures within a range of vaporization and decomposition temperatures of the first zirconium chelate complex and the second zirconium chelate complex in the raw material solution, controllability of the film composition is improved when a film is formed using the raw material solution.

In the raw material solution of the present invention, a mixing ratio of first and second zirconium chelate complexes, that is, a mixing ratio of a first zirconium chelate complex $C_1$ with a second zirconium chelate complex $C_2$, ($C_1/C_2$), may be from 10/90 to 90/10 in terms of molar ratio.

By controlling the molar ratio in the above range, vaporization and decomposition temperatures of the zirconium chelate complexes contained in the raw material solution can be controlled.

In the raw material solution of the present invention, the first and second zirconium chelate complexes may be complexes selected from the group consisting of Zr(dhd)$_4$, Zr(thd)$_4$, tetrakisacetylacetonate zirconium (hereinafter referred to as Zr(acac)$_4$), tetrakishexafluoroacetylacetonate zirconium (hereinafter referred to as Zr(hfac)$_4$), tetrakistrifluoroacetylacetonate zirconium(hereinafter referred to as Zr(tfac)$_4$), tetrakistrimethyloctanedionate zirconium (hereinafter referred to as Zr(tod)$_4$) and tetrakisdiphenylpropanedionate zirconium (hereinafter referred to as Zr(dppd)$_4$).

In the raw material solution of the present invention, the first zirconium chelate complex may be Zr(thd)$_4$ and the second zirconium chelate complex may be Zr(dhd)$_4$.

The raw material solution containing Zr(thd)$_4$ as the first zirconium chelate complex and Zr(dhd)$_4$ as the second zirconium chelate complex has a low decomposition temperature compared to a Zr(dhd)$_4$ complex, and therefore the raw material solution is less likely to react with Pb(thd)$_4$ even when mixed therewith.

In the raw material solution of the present invention, the organic solvent may comprise one, or at least two kinds of solvents selected from the group consisting of tetrahydrofuran (hereinafter referred to as THF), methyltetrahydrofuran (hereinafter referred to as Me-THF), n-octane, isooctane, hexane, cyclohexane (hereinafter referred to as CyHex), pyridine, lutidine, butyl acetate and amyl acetate.

The raw material solution of the present invention may further contain at least one of an organolead compound and an organotitanium compound.

When the raw material solution further contains at least one of an organolead compound and an organotitanium compound, the ligands in the organozirconium composite and the the organolead composite, or the ligands in the organozirconium composite and the organotitanium composite may cause ligand exchange in the raw material solution to form plural kinds of lead or titanium complexes containing at least two kinds of ligands, and to form a compound in which the coordination numbers vary depending on the respective complexes. Therefore, the controllability of the composition in terms of lead or titanium may be improved.

Also the present invention provides a method of forming a PZT dielectric thin film, which comprises forming the film using the organozirconium composite of the present invention, the organozirconium composite obtained by the synthesis method of the present invention, or the raw material solution of the present invention.

Since the organozirconium composite and the raw material solution containing the organozirconium composite of the present invention are controlled to a temperature which is near the respective decomposition temperatures of an organolead compound and an organotitanium compound as the other raw material of a PZT thin film, a PZT thin film can be formed from a smaller feed amount of the organozirconium composite than conventionally.

DETAILED DESCRIPTION OF THE PREFERRED EMBODIMENTS

Figure 1:
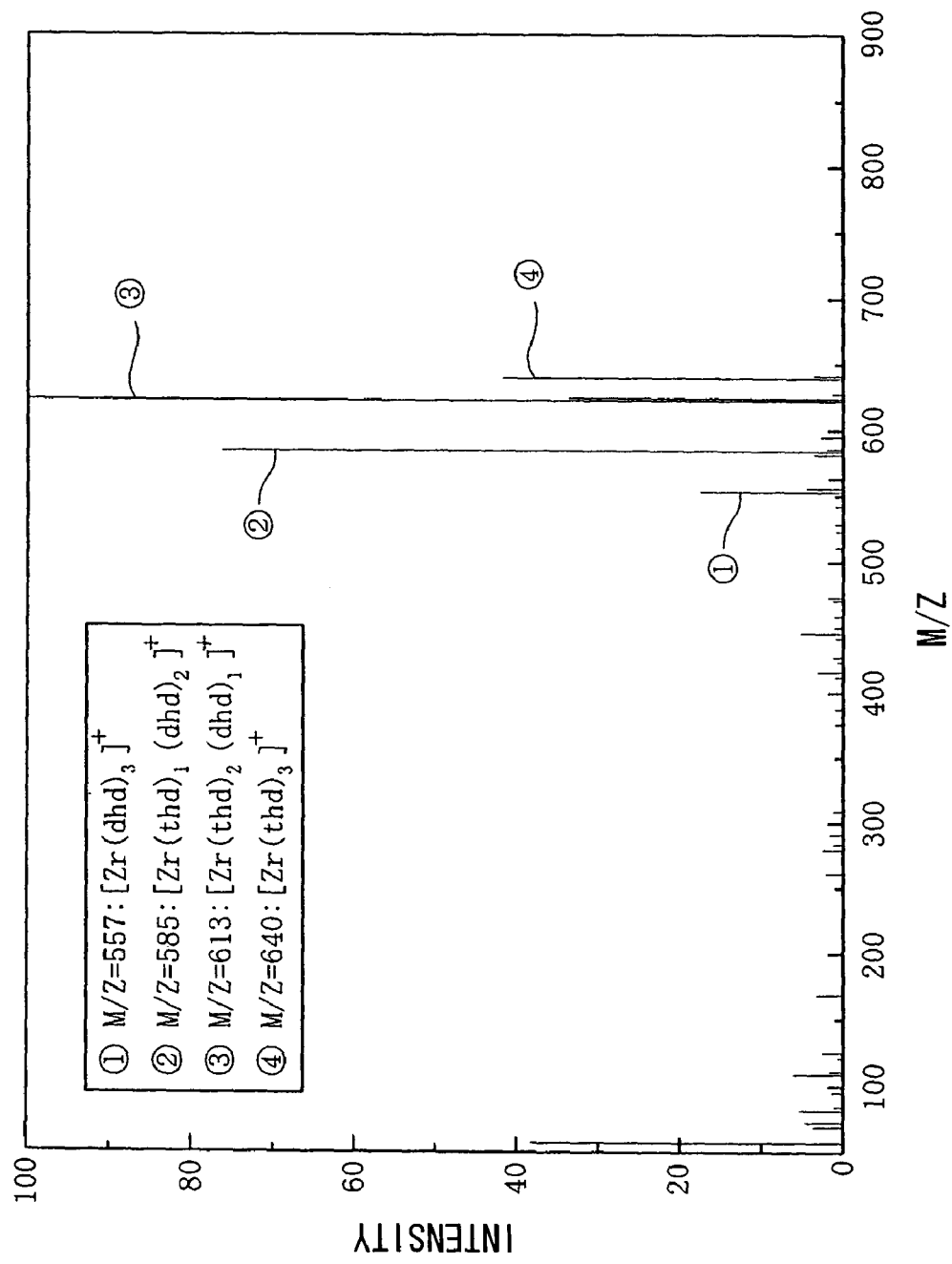
FIG. 1 is a graph showing a mass spectrum of an organozirconium composite of the present invention.

The embodiments of the present invention will now be described.

The organozirconium composite of the present invention contains one, or at least two kinds of zirconium chelate complexes containing, as a ligand, both of a first β diketone and a second β diketone having a structure different from that of the first β diketone. The characteristics constitution of the present invention is that, when the organozirconium composite includes at least two kinds of zirconium chelate complexes, the coordination numbers of the first β diketone and the second β diketone that coordinate to at least two kinds of zirconium chelate complexes vary depending on the respective zirconium chelate complexes. The organozirconium composite including one or more kinds of zirconium chelate complexes containing both of a first β diketone and a second β diketone as a ligand has a decomposition temperature which is near the respective decomposition temperatures of an organolead compound and an organotitanium compound compared to a conventional organozirconium composite. Therefore, when a film is formed by the MOCVD method using an organozirconium composite containing at least this complex as a material, the composition of a PZT thin film can be more precisely controlled over a broad temperature range. Since the organozirconium composite, which contains at least two kinds of zirconium chelate complexes in which the coordination number of the first β diketone coordinates and the coordination number of the second β diketone vary depending on the respective zirconium chelate complexes, has a decomposition temperature which is near the respective decomposition temperatures of an organolead compound and an organotitanium compound, the composition of a PZT thin film can be more precisely controlled over a broad temperature range.

In the zirconium chelate complex contained in the organozirconium composite of the present invention, β diketone coordinates in such a manner that all eight coordination sites of metallic zirconium as a center metal are occupied. Therefore, the zirconium chelate complex is a stable compound compared to a complex containing an alkoxide in a ligand and is less likely to form a complex, which is difficult to vaporize, even when mixed with an organolead compound such as $Pb(thd)_2$.

The organozirconium composite of the present invention may further contain at least one of a first β diketone ligand and a second β diketone ligand, and may also include at least one of a zirconium chelate complex containing only a first β diketone ligand as a ligand and a zirconium chelate complex containing only a second β diketone ligand as a ligand.

The first β diketone and the second β diketone are preferably compounds selected from the group consisting of thd, dhd, acac, hfac, tfac, tod and dppd, and more preferably a combination of thd as the first β diketone and dhd as the second β diketone, or a combination of thd as the first β diketone and acac as the second β diketone.

The zirconium chelate complex contained in the organozirconium composite of the present invention is obtained by reacting at least two kinds of β diketone compounds with a zirconium compound. By coordinating at least two kinds of β diketone compounds to metallic zirconium, it is made possible to lower the decomposition temperature compared to a commonly used zirconium chelate complex in which only one kind of a β diketone compound is coordinated, for example, a $Zr(thd)_4$ complex. Therefore, it is made possible to obtain the decomposition temperature which is near the decomposition temperatures of the organolead compound and the organotitanium compound used in the other PZT thin film and to make the control of the composition of the PZT thin film easy.

The organozirconium composite of the present invention is less likely to form a composite which is difficult to vaporize, for example, a composite of zirconium and lead even when mixed with an organolead compound. Therefore, even when a film is formed by the MOCVD method, the compound is not left as a residue. The ligand to be coordinated in the zirconium chelate complex of the present invention is only a β diketone compound. The β diketone compound include at least two kinds and the upper limit of the number of kinds is selected from the valence (coordination number) of a complex metal. Two kinds of β diketone compounds are preferable.

In the case of a zirconium chelate complex obtained by reacting two kinds of β diketone compounds with a zirconium compound, a mixing ratio of two kinds of β diketone compounds, that is, a mixing ratio of one β diketone compound A with the other β diketone compound B, (A/B), is controlled from 80/20 to 20/80 in terms of molar ratio. Two or more kinds of β diketone compounds are selected from the group consisting of Hdhd, Hthd, Hacac, Hhfac, Htfac, Htod and Hdppd. In the case in which two kinds of β diketone compounds are coordinated, one β diketone compound is preferably Hdhd and the other β diketone compound is preferably Hthd.

The method of synthesizing a first organozirconium composite of the present invention will now be described.

The organozirconium composite of the present invention is obtained by mixing a first β diketone compound with a zirconium chelate complex containing, as a ligand, a second β diketone having a structure different from that of the first β diketone. In the case in which the organozirconium composite is synthesized, the amount of the first β diketone compound is controlled within a range from 100 to 1600 mol % based on the zirconium chelate complex containing the second β diketone as a ligand. When the amount is less than 100 mol %, characteristics of the zirconium chelate complex containing the second β diketone as a ligand are prominent and, when the amount exceeds 1600 mol %, characteristics of the β diketone compound are prominent. Therefore, the decomposition temperature decreases compared to an organotitanium compound such as $Ti(iPrO)_2(thd)_2$ and it becomes difficult to control the composition of the film and also the decomposition temperature increases compared to the organotitanium compound, and thus the temperature shifts from the film forming temperature. A combination of Hthd as the first β diketone compound and $Zr(dhd)_4$ as the zirconium chelate complex containing, as a ligand, the second β diketone compound, and a combination of Hdhd as the first β diketone compound and $Zr(thd)_4$ as the zirconium chelate complex containing, as a ligand, the second β diketone compound, are preferable.

The first synthesis method using a combination of Hthd and $Zr(dhd)_4$ will now be described. First, $Zr(dhd)_4$ is dissolved in a solvent to prepare a 15–30 wt % solution. Examples of the solvent include one, or at least two kinds of organic compounds selected from the group consisting of n-hexane, toluene, THF, octane and xylene. The dissolution may be conducted at room temperature under normal pressure. Then, Hthd is dissolved in the solution in an amount of 100 to 1600 mol % based on $Zr(dhd)_4$ and the mixture is reacted at room temperature for 12 hours. In this reaction, the β diketone compound causes ligand exchange with the ligand in the chelate complex and the degree of ligand exchange can vary with the mixing ratio. Then, the solvent is removed by drying the reaction solution under reduced pressure to obtain an organozirconium composite containing plural zirconium chelate complexes in which the coordination number of dhd and the coordination number of thd vary depending on the respective complexes. When using n-hexane as a solvent, the solvent is preferably removed at 70° C. under about 1330 Pa (10 Torr). It is estimated that plural zirconium chelate complexes mainly contain $Zr(dhd)_3(thd)$, $Zr(dhd)_2(thd)_2$ and $Zr(dhd)(thd)_3$ and also contains dimers of the zirconium chelate complexes. The resulting organozirconium complex contains Hdhd produced by the reaction and also contains unreacted Hthd and $Zr(dhd)_4$ and a hyperreactive substance $Zr(thd)_4$ according to the mixing ratio of Hthd with $Zr(dhd)_4$.

The second synthesis method using a combination of Hthd and $Zr(dhd)_4$ will now be described. In the second synthesis method, the reaction solution is concentrated by heating under reduced pressure until the amount of the solvent is reduced to half, and then the resulting concentrated solution is recrystallized by air-cooling to room temperature. Subsequently, the β diketone compound produced by the reaction and the unreacted substance are removed. After removing the unreacted substance, the resulting solution is dried under reduced pressure to obtain an organozirconium composite including plural zirconium chelate complexes in which the coordination number of dhd and the coordination number of thd vary depending on the respective complexes.

The method of synthesizing a second organozirconium composite of the present invention will now be described.

First, a starting material of a zirconium chelate complex is dissolved in a solvent. The starting material is dissolved in the solvent to prepare a 15–30 wt % solution. As the starting material, zirconium compounds are selected from the group consisting of zirconium butoxide, zirconium chloride and zirconium chloride oxide. Examples of the solvent include one, or at least two kinds of organic solvents selected from the group consisting of toluene, THF, hexane, octane and xylene.

Then, a mixed solution containing at least two kinds of β diketone compounds is added to the solution. Two or more kinds of β diketone compounds are added in a total amount of 4 moles per mole of valence of metallic zirconium. In the case in which a zirconium chelate complex is synthesized by reacting at least two kinds of β diketone compounds with a zirconium compound, a mixing ratio of two kinds of β diketone compounds, that is, a mixing ratio of one β diketone compound A with the other β diketone compound B, (A/B), is controlled from 80/20 to 20/80 in terms of molar ratio. Two or more kinds of β diketone compounds are selected from the group consisting of Hdhd, Hthd, Hacac, Hhfac, Htfac, Htod and Hdppd. In the case in which two kinds of β diketone compounds are coordinated, one β diketone compound is preferably Hdhd and the other β diketone compound is preferably Hthd.

Then, a mixed solution prepared by adding the mixed solution containing at least two kinds of β diketone compounds is refluxed by heating at a temperature higher than the boiling point of an organic solvent contained in the solution for 2 to 5 hours, and preferably for 5 hours. As a result of heating under reflux, the residual moisture and OH groups are removed by azeotropy and a crystal is obtained as a synthetic after concentration. Since this crystal as a synthetic is a crude crystal, a purified crystal of a zirconium chelate complex can be obtained by repeating a purification process of recrystallizing using an organic solvent, vaporizing the solvent under reduced pressure and drying.

The organozirconium composite obtained by using Hdhd and Hthd as the β diketone compound and using zirconium butoxide as the zirconium compound was subjected to thermogravimetry. The results of mass spectrum are shown in FIG. 1.

As is apparent from FIG. 1, taking notice of peaks at m/Z of 585 and 613, a compound in which clearly different ligands are coordinated to one zirconium is produced. Taking notice of a cleaved compound, ions having m/z of 640, ions having m/z of 613, ions having m/z of 585 and ions having m/z of 557 respectively suggest that $Zr(thd)_3(dhd)$ or $Zr(thd)_4$, $Zr(thd)_2(dhd)_2$ or $Zr(thd)_3(dhd)$, $Zr(thd)(dhd)_3$ or $Zr(thd)_2(dhd)_2$ and $Zr(dhd)_4$ or $Zr(thd)(dhd)_3$ exist in the sample to be analyzed. This fact shows that plural zirconium chelate complexes each containing a different ligand are produced.

The first raw material solution of the present invention obtained by dissolving the organozirconium composite thus obtained of the present invention can precisely control the composition of a PZT thin film over a broad temperature range. As the organic solvent used in the raw material solution, one, or at least two kinds of solvents selected from the group consisting of THF, Me-THF, n-octane, iso-octane, hexane, CyHex, pyridine, lutidine, butyl acetate and amyl acetate can be used.

The second raw material solution of the present invention is prepared by mixing a first zirconium chelate complex in which a single kind of a β diketone compound is coordinated to a center metal and a second zirconium chelate complex in which a single kind of a β diketone compound different from the β diketone compound is coordinated to a center metal in an organic solvent.

In the raw material solution thus prepared, a portion of ligands of the first zirconium chelate complex and a portion of ligands of the second zirconium chelate complex in the raw material solution cause ligand exchange. As a result, it is made possible for the vaporization temperature to be within a range of the vaporization temperatures of the first zirconium chelate complex and the second zirconium chelate complex. The vaporization temperature can be optionally controlled within the vaporization temperatures of the first zirconium chelate complex and the second zirconium chelate complex by controlling the mixing ratio of the first zirconium chelate complex with the second zirconium chelate to arbitrary ratio. For example, when the first zirconium chelate complex is $Zr(thd)_4$ and the second zirconium chelate is $Zr(dhd)_4$, the vaporization temperature of the zirconium chelate complex contained in the raw material solution of the present invention is within a range from the respective vaporization temperatures of $Zr(thd)_4$ and $Zr(dhd)_4$.

It is also made possible for the decomposition temperature to be within the range of the decomposition temperatures of the first zirconium chelate complex and the second zirconium chelate complex. The decomposition temperature can be controlled by the mixing ratio of the first zirconium chelate complex with the second zirconium chelate complex. The decomposition temperature can be optionally controlled within the range of the decomposition temperatures of the first zirconium chelate complex and the second zirconium chelate complex by controlling the mixing ratio of the first zirconium chelate complex with the second zirconium chelate complex in the raw material solution.

In the first and second zirconium chelate complexes used in the raw material solution of the present invention, since a single kind of a β diketone compound coordinates to a center metal, all eight coordination sites of zirconium are occupied. In the case of the zirconium chelate complex produced by ligand exchange, all eight coordination sites of zirconium are occupied as well. Therefore, similar to the above-described organozirconium complex, it is difficult to form a complex, which is difficult to vaporize with $Pb(thd)_2$ even when mixed the raw material solution with $Pb(thd)_2$.

In the case in which the raw material solution of the present invention further contains at least one of an organolead compound such as $Pb(thd)_2$ and an organotitanium compound such as $Ti(iPrO)_2(thd)_2$, the ligands in the organozirconium composite and the the organolead composite, or the ligands in the organozirconium composite and the organotitanium composite may cause ligand exchange in the raw material solution to form plural kinds of lead or titanium complexes containing at least two kinds of ligands, and to form a compound in which the coordination numbers vary depending on the respective complexes. Therefore, the controllability of the composition in terms of lead or titanium may be improved.

A mixing ratio of first and second zirconium chelate complexes, that is, a mixing ratio of a first zirconium chelate complex $C_1$ with a second zirconium chelate complex $C_2$, $(C_1/C_2)$, is controlled from 10/90 to 90/10 in terms of molar ratio. A preferable molar ratio is from 50/50 to 80/20. In the case in which the molar ratio is less than 10/90, that is, the content of $C_1$ is small, there arise drawbacks in that characteristics becomes the same as those of the second zirconium chelate complex $C_2$. In the case in which the molar ratio exceeds 90/10, that is, the content of $C_1$ is large, there arise drawbacks in that characteristics becomes the same as those of the second zirconium chelate complex $C_1$. The first and second zirconium chelate complexes are selected from the group consisting of $Zr(dhd)_4$, $Zr(thd)_4$, $Zr(acac)_4$, $Zr(hfac)_4$, $Zr(tfac)_4$, $Zr(tod)_4$ and $Zr(dppd)_4$. It is preferable that the first zirconium chelate complex be $Zr(thd)_4$ and the second zirconium chelate complex be $Zr(dhd)_4$.

As the organic solvent, the same solvent as in the case of the above-described first raw material solution is used. A mixing ratio of the first zirconium chelate complex with the second zirconium chelate complex is not specifically limited as long as these complexes may be sufficiently dissolved when using in MOCVD.

The raw material solution containing the organozirconium composite of the present invention may be prepared by mixing the first zirconium chelate complex and the second zirconium chelate complex in an organic solvent in a reaction vessel or a closed vessel, or the raw material solution containing the organozirconium composite of the present invention may be prepared by enclosing a first raw material solution, which is prepared by dissolving a first zirconium chelate complex in an organic solvent, into a first closed vessel, similarly enclosing a second raw material solution, which is prepared by dissolving a second zirconium chelate complex in an organic solvent, into a second closed vessel, and feeding the first and second raw material solutions into a MOCVD apparatus, thereby to mix the respective raw material solutions in a mixing chamber prior to a vaporization chamber.

In the present embodiment, the raw material solution was prepared by mixing the first zirconium chelate complex and the second zirconium chelate complex in the organic solvent. In the present invention, the raw material solution may be prepared by mixing three or more kinds of zirconium chelate complexes in the organic solvent in place of at least two kinds of zirconium chelate complexes.

Figure 9:
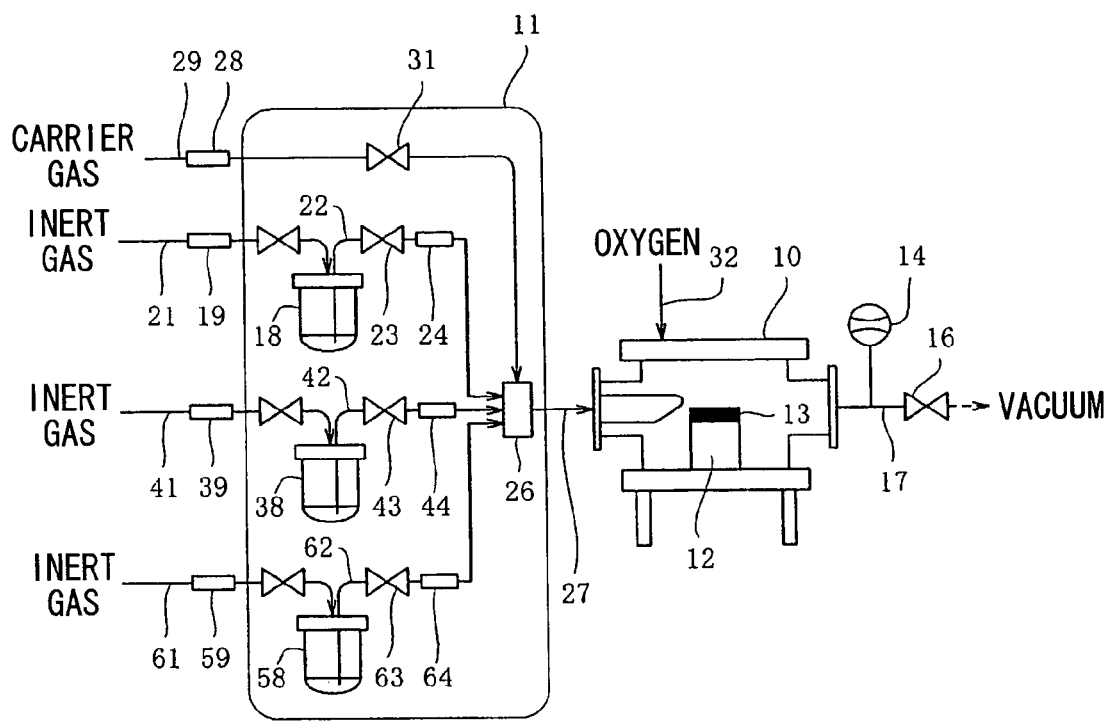
FIG. 9 is a block diagram of a common MOCVD apparatus.

To form a film of the organozirconium composite and the raw material solution on a substrate, the MOCVD apparatus shown in FIG. 9 is used.

As shown in FIG. 9, the MOCVD apparatus is equipped with a film forming chamber 10 and a vapor generating device 11. In the film forming chamber 10, a heater 12 is provided and a substrate 13 is held on the heater 12. The inside of the film forming chamber 10 is evacuated through a piping 17 equipped with a pressure gage 14 and a needle valve 16. To the film forming chamber 10, an oxygen introducing pipe 32 is connected. The vapor generating device 11 is equipped with a raw material container 18 for accommodating a raw material solution containing an organozirconium composite of the present invention. To the raw material container 18, a pressurizing inert gas introducing pipe 21 is connected through a gas flow rate control device 19, and a feed pipe 22 is also connected. The feed pipe 22 is equipped with a needle valve 23 and a mass flow controller 24 and the feed pipe 22 is connected to a vaporization chamber 26.

Also the MOCVD apparatus is equipped with raw material containers 38 and 58 for accommodating a raw material solution containing an organolead compound and a raw material solution containing an organotitanium compound, and pipings are connected with the same arrangement and are respectively connected to the vaporization chamber 26. To the vaporization chamber 26, a carrier gas introducing pipe 29 is connected through a needle valve 31 and a gas flow rate control device 28. The vaporization chamber 26 is further connected to the film forming chamber 10 through a piping 27.

In this apparatus, a pressurizing inert gas is introduced into the raw material container 18 through the introducing pipe 21 and the raw material solution accommodated in the raw material container 18 is transported to the vaporization chamber 26 through the feed pipe 22. The organolead compound, the organozirconium composite and the organotitanium compound, which were converted into vapors as a result of vaporization in the vaporization chamber 26, are further fed into the film forming chamber 10 through a piping 27 by means of a carrier gas introduced into the vaporization chamber 26 from the carrier gas introducing pipe 29. In the film forming chamber 10, vapors of the organolead compound, the organozirconium composite and the organotitanium compound are thermally decomposed, together with oxygen introduced through the oxygen introducing pipe 32, and then accumulated on the heated substrate 13 to form a PZT dielectric thin film. Examples of the pressurizing inert gas and the carrier gas include argon, helium and nitrogen.

EXAMPLES

The following Examples and Comparative Examples further illustrate the present invention in detail.

Example 1

First, $Zr(dhd)_4$ was prepared as a zirconium chelate complex and Hthd was prepared as a β diketone compound, respectively. Then, $Zr(dhd)_4$ was dissolved in a solvent at room temperature under normal pressure to prepare a 15–30 wt % solution. As the solvent, n-hexane was used. Then, Hthd was added to the solution in an amount of 100 mol % based on $Zr(dhd)_4$ and the mixture was reacted at room temperature for about 12 hours while stirring. The resulting reaction solution was dried under reduced pressure to remove the solvent, thereby obtaining an organozirconium composite containing plural zirconium chelate complexes in which the coordination number of dhd and the coordination number of thd vary depending on the respective zirconium chelate complexes, unreacted $Zr(dhd)_4$ and Hthd, and $Zr(dhd)_4$ and Hdhd.

Example 2

In the same manner as in Example 1, except for synthesizing by mixing so that the amount of Hthd is controlled to 400 mol % based on $Zr(dhd)_4$, an organozirconium composite was obtained.

Example 3

In the same manner as in Example 1, except for synthesizing by mixing so that the amount of Hthd is controlled to 1600 mol % based on $Zr(dhd)_4$, an organozirconium composite was obtained.

Example 4

First, $Zr(dhd)_4$ was prepared as a zirconium chelate complex and Hthd was prepared as a β diketone compound, respectively. Then, $Zr(dhd)_4$ was dissolved in a solvent at room temperature under normal pressure to prepare a 15–30 wt % solution. As the solvent, n-hexane was used. Then, Hthd was added to the solution in an amount of 100 mol % based on $Zr(dhd)_4$ and the mixture was reacted at room temperature for about 12 hours while stirring. The resulting reaction solution was concentrated under reduced pressure until the amount of the solvent was reduced to about half and the concentrated solution was recrystallized by air cooling to room temperature. Subsequently, the unreacted substance was removed by discarding the supernatant and the concentrated solution was dried under reduced pressure to obtain an organozirconium composite including zirconium chelate complexes in which the coordination number of dhd and the coordination number of thd vary depending on the respective zirconium chelate complexes.

Example 5

In the same manner as in Example 4, except for synthesizing by mixing so that the amount of Hthd is controlled to 400 mol % based on $Zr(dhd)_4$, an organozirconium composite was obtained.

Example 6

In the same manner as in Example 4, except for synthesizing by mixing so that the amount of Hthd is controlled to 1600 mol % based on $Zr(dhd)_4$, an organozirconium composite was obtained.

Example 7

In the same manner as in Example 1, except for replacing the zirconium chelate complex by $Zr(thd)_4$ and the β diketone compound by Hdhd and synthesizing by mixing so that the amount of Hdhd is controlled to 100 mol % based on $Zr(thd)_4$, an organozirconium composite was obtained.

Example 8

In the same manner as in Example 7, except for synthesizing by mixing so that the amount of Hdhd is controlled to 400 mol % based on $Zr(thd)_4$, an organozirconium composite was obtained.

Example 9

In the same manner as in Example 7, except for synthesizing by mixing so that the amount of Hdhd is controlled to 1600 mol % based on $Zr(thd)_4$, an organozirconium composite was obtained.

Example 10

In the same manner as in Example 4, except for replacing the zirconium chelate complex by $Zr(thd)_4$ and the β diketone compound by Hdhd and synthesizing by mixing so that the amount of Hdhd is controlled to 100 mol % based on $Zr(thd)_4$, an organozirconium composite was obtained.

Example 11

In the same manner as in Example 10, except for synthesizing by mixing so that the amount of Hdhd is controlled to 400 mol % based on $Zr(thd)_4$, an organozirconium composite was obtained.

Example 12

In the same manner as in Example 10, except for synthesizing by mixing so that the amount of Hdhd is controlled to 1600 mol % based on $Zr(thd)_4$, an organozirconium composite was obtained.

Comparative Example 1

First, a $Zr(nBuO)_4$ complex was used as a starting material of a zirconium material and the staring material was dissolved in toluene as an organic solvent to prepare a 20–27 wt % solution. Then, Hdhd was added to the solution in an amount of 4 moles per mole of the $Zr(nBuO)_4$ complex and the mixture was reacted by heating under reflux at 110° C. for 2 hours. Toluene in the reaction solution was removed under reduced pressure to obtain a crude product. Then, the resulting crude product was recrystallized in hexane to obtain a purified crystal made of a $Zr(dhd)_4$ complex.

Comparative Example 2

First, a $Zr(nBuO)_4$ complex was used as a starting material of a zirconium material and the starting material was dissolved in toluene as an organic solvent to prepare a 20–27 wt % solution. Then, Hthd was added to the solution in an amount of 4 moles per mole of the $Zr(nBuO)_4$ complex and the mixture was reacted by heating under reflux at 110° C. for 2 hours. Toluene in the reaction solution was removed under reduced pressure to obtain a crude product. Then, the resulting crude product was recrystallized in hexane to obtain a purified crystal made of a $Zr(thd)_4$ complex.

Comparative Example 3

First, a $Zr(tBuO)_4$ complex was used as a starting material of a zirconium material and the starting material was dissolved in toluene as an organic solvent to prepare a 20–27 wt % solution. Then, Hthd was added to the solution in an amount of 2 moles per mole of the $Zr(tBuO)_4$ complex and the mixture was reacted by heating under reflux at 110° C. for 4 hours. Toluene in the reaction solution was removed under reduced pressure to obtain a crude product. Then, the resulting crude product was recrystallized in hexane to obtain a purified crystal made of a $Zr(tBuO)_2(thd)_2$ complex.

Comparative Example 4

In the same manner as in Comparative Example 8, except for replacing the $Zr(tBuO)_4$ complex by a $Zr(tAmylO)_4$ complex, synthesis was conducted to obtain a $Zr(tAmylO)_2(thd)_2$ complex.

Comparative Example 5

First, a $Zr(iPrO)_4$ complex was used as a starting material of a zirconium material and the starting material was dissolved in toluene as an organic solvent to prepare a 20–27 wt % solution. Then, Hthd was added to the solution in an amount of I mole per mole of the $Zr(iPrO)_4$ complex and the mixture was reacted by heating under reflux at 110° C. for 4 hours. Toluene in the reaction solution was removed under reduced pressure to obtain a crude product. Then, the resulting crude product was recrystallized in hexane to obtain a purified crystal made of a $Zr_2(iPrO)_6(thd)_2$ complex.

Comparative Example 6

First, a $Zr(iPrO)_4$ complex was used as a starting material of a zirconium material and the starting material was dissolved in toluene as an organic solvent to prepare a 20–27 wt % solution. Then, Hthd was added to the solution in an amount of 3 moles per mole of the $Zr(iPrO)_4$ complex and the mixture was reacted by heating under reflux at 110° C. for 4 hours. Toluene in the reaction solution was removed under reduced pressure to obtain a crude product. Then, the resulting crude product was recrystallized in hexane to obtain a purified crystal made of a $Zr(iPrO)(thd)_3$ complex.

Comparative Evaluation 1

Figure 2:
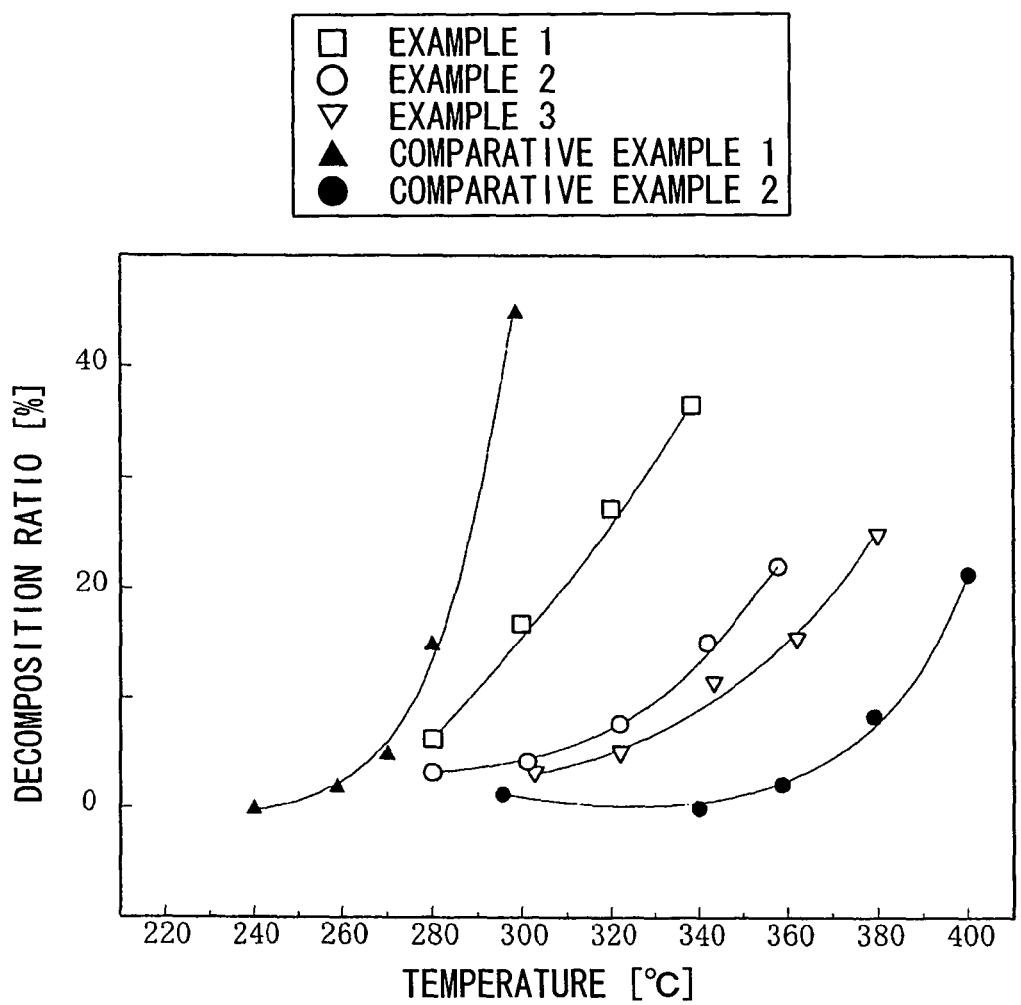
FIG. 2 is a graph showing relationships between the heating temperature and the decomposition ratio in Examples 1 to 3 and Comparative Examples 1 and 2.
Figure 3:
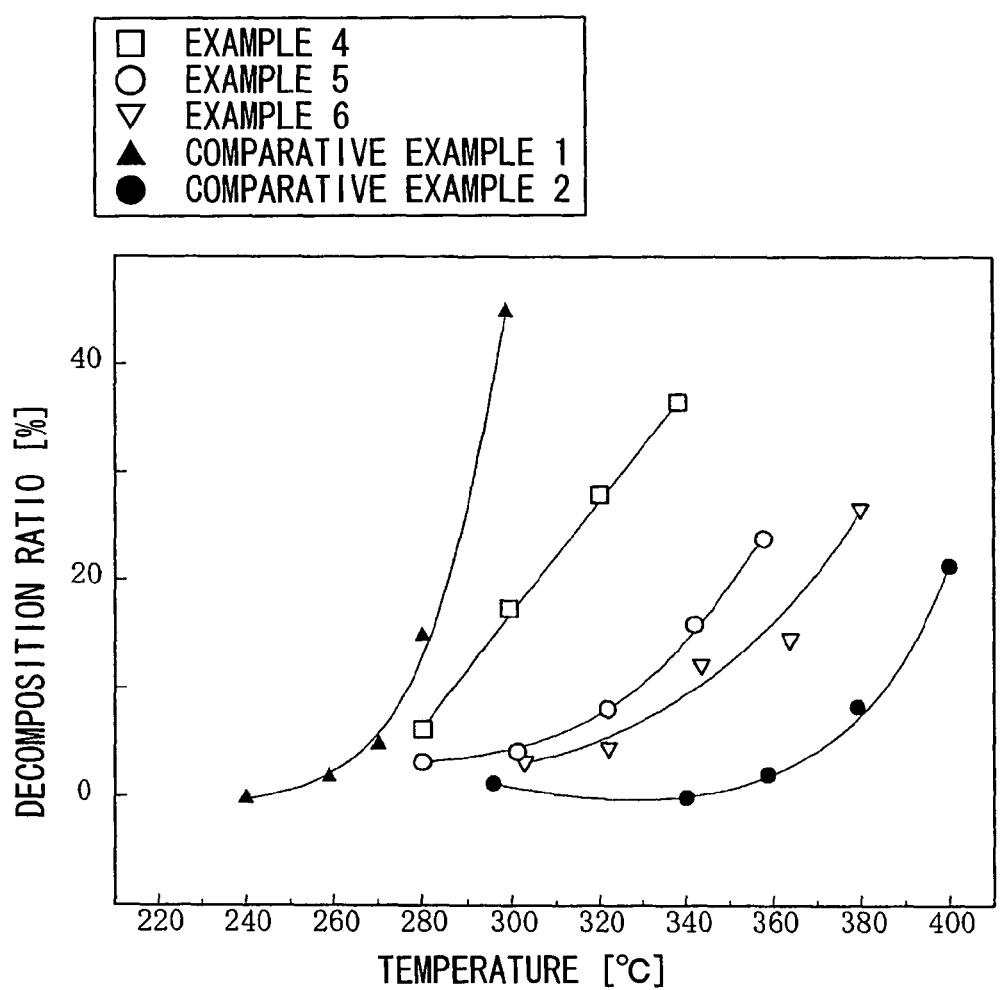
FIG. 3 is a graph showing relationship between the heating temperature and the decomposition ratio in Examples 4 to 6 and Comparative Examples 1 and 2.
Figure 4:
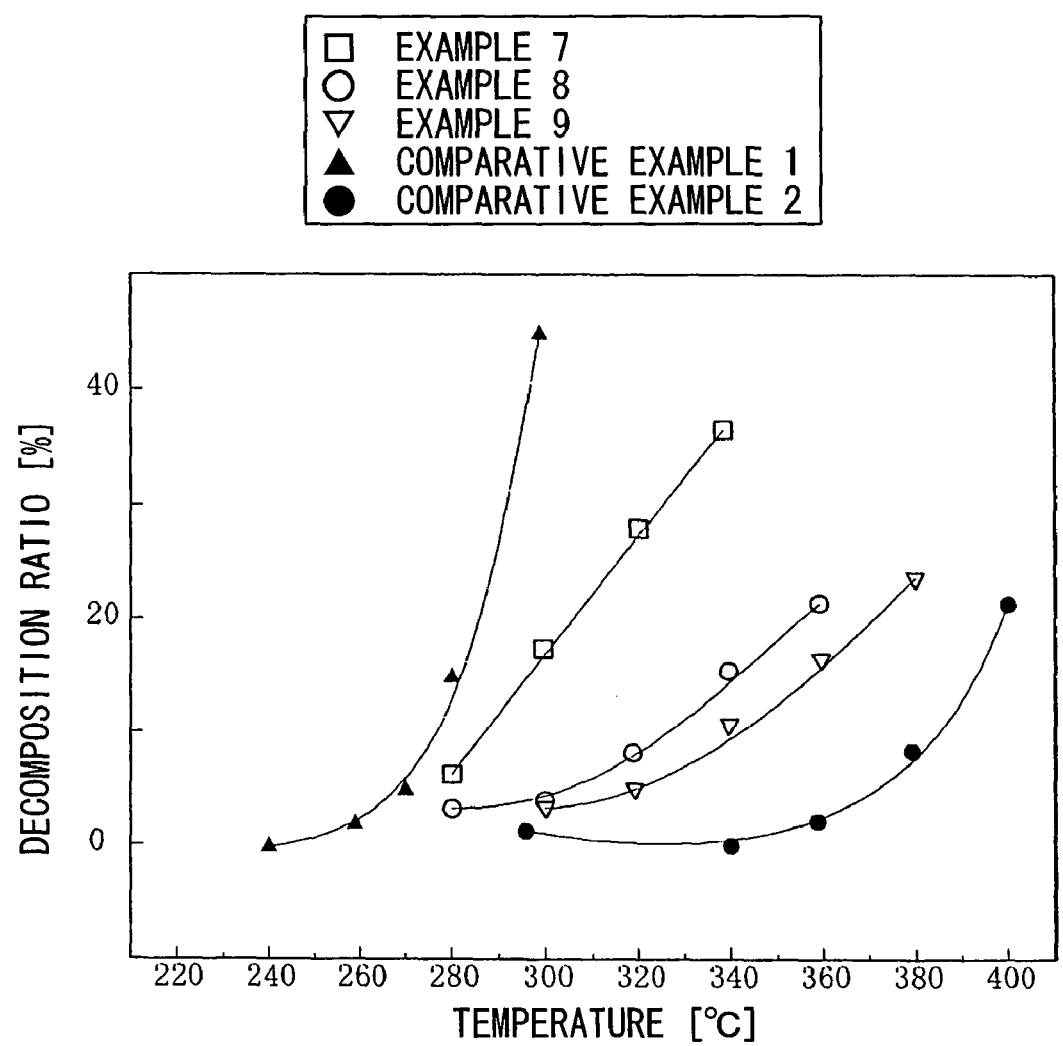
FIG. 4 is a graph showing relationships between the heating temperature and the decomposition ratio in Examples 7 to 9 and Comparative Examples 1 and 2.
Figure 5:
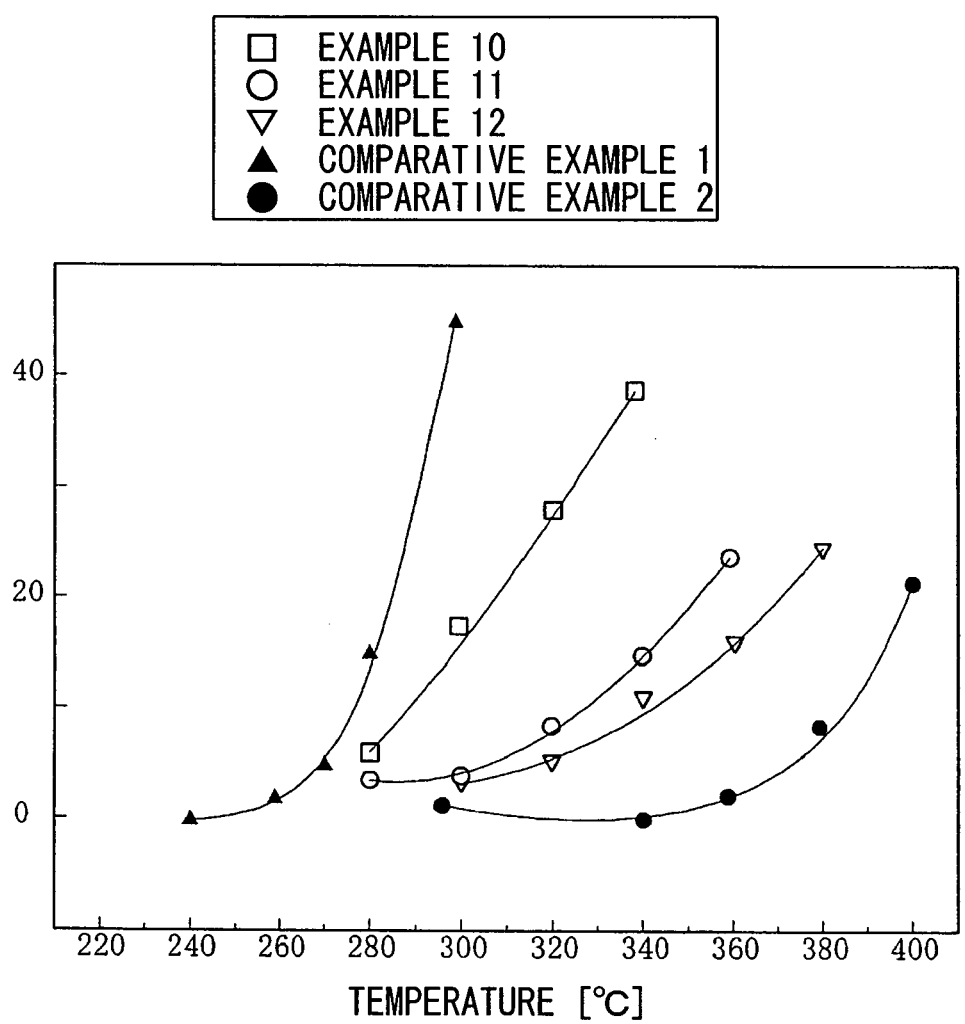
FIG. 5 is a graph showing relationships between the heating temperature and the decomposition ratio in Examples 10 to 12 and Comparative Examples 1 and 2.

The organozirconium composites obtained in Examples 1 to 12 and the zirconium chelate complexes of Comparative Examples 1 and 2 were heated to an arbitrary temperature and each decomposition ratio was measured. The results of Examples 1 to 3 are shown in FIG. 2, the results of Examples 4 to 6 are shown in FIG. 3., the results of Examples 7 to 9 are shown in FIG. 4, and the results of Examples 10 to 12 are shown in FIG. 5. Also the results of Comparative Examples 1 and 2 are shown in FIG. 2 to FIG. 5.

As is apparent from FIG. 2 to FIG. 5, the decomposition temperatures of the organozirconium composites of Examples 1 to 12 are within the range of the decomposition temperatures of the zirconium chelate complexes of Comparative Examples 1 and 2 and therefore both of Examples 1 to 6 and Examples 7 to 12, which are synthesized by different synthesis methods, exhibit the same decomposition characteristics. It is also apparent that the decomposition temperature can be controlled by changing the amount of the β diketone compound added upon synthesis. As is apparent from these results, the organozirconium composite of the present invention can be controlled to a decomposition temperature which is near the decomposition temperature 325° C. of $Pb(thd)_2$ and the decomposition temperature 320° C. of $Ti(tBuO)_2(thd)_2$.

Comparative Evaluation 2

The organozirconium composites of Examples 2, 5, 9 and 12 and the zirconium chelate complexes of Comparative Examples 3 to 6 were divided into two portions. Each of one portion was mixed with $Pb(thd)_2$ in an inert atmosphere and the mixture was dissolved in THF to prepare a raw material solution, while each of the other portion was mixed with $Pb(thd)_2$ in an inert atmosphere and the mixture was dissolved in cyclohexane to prepare a raw material solution.

These raw material solutions were stored in an inert atmosphere while being shielded from light for one month. After the completion of storing, the respective solvents were removed under reduced pressure and the organozirconium composites of Examples 2, 5, 9 and 12 and the zirconium chelate complexes of Comparative Examples 3 to 6 were subjected to thermogravimetry (TG). A change in vaporization residue ratio before and after mixing with $Pb(thd)_2$ is shown in Table 1.

TABLE 1

| | Organic solvent | Vaporization residue ratio [% by weight] | |
|---|---|---|---|
| | | Before mixing | After mixing |
| Example 2 | THF | 1.6 | 2.1 |
| | CyHex | 1.6 | 2.3 |
| Example 5 | THF | 1.7 | 2.0 |
| | CyHex | 1.7 | 2.2 |
| Example 9 | THF | 1.6 | 2.0 |
| | CyHex | 1.6 | 2.3 |
| Example 12 | THF | 1.6 | 2.3 |
| | CyHex | 1.6 | 2.5 |
| Comparative Example 3 | THF | 7.5 | 26.2 |
| | CyHex | 7.5 | 27.6 |
| Comparative Example 4 | THF | 7.2 | 21.5 |
| | CyHex | 7.2 | 22.4 |
| Comparative Example 5 | THF | 6.8 | 31.5 |
| | CyHex | 6.8 | 32.3 |
| Comparative Example 6 | THF | 9.5 | 15.5 |
| | CyHex | 9.5 | 16.7 |

As is apparent from Table 1, in the case in which Comparative Example 3 and Comparative Example 5 are mixed with $Pb(thd)_2$, the vaporization residue drastically increased after storage for one month, while a drastic increase in vaporization residue was not observed in Examples 2, 5, 9 and 12. The reason is believed to be as follows. That is, in the cases of the organozirconium composites of Examples 2, 5, 9 and 12, all eight coordination sites of zirconium are occupied and high stability can be maintained, while in the cases of the zirconium chelate complexes containing an alkoxide such as $Zr_2(iPrO)_6(thd)_2$ or $Zr(iPrO)(thd)_3$ of Comparative Examples 5 and 6, merely six or seven coordination sites in all coordination sites of zirconium are occupied and all coordination sites cannot be occupied; therefore, the stability of the compound is degraded compared to the compounds in which all coordination sites are occupied, and thus the complexes react with surrounding $Pb(thd)_2$ to form a vaporization residue in large amounts. Also it is believed that Pb alkoxide was formed. The amount of the vaporization residue did not vary drastically depending on the kind of the organic solvent.

Example 13

First, a $Zr(nBuO)_4$ complex was used as a starting material of a zirconium material and the starting material was dissolved in THF as a solvent to prepare a 15–25 wt % solution. Then, as a mixed solution containing a β diketone compound, a mixed solution containing Hdhd and Hthd in a molar ratio of 75/25, that is, a mixed solution containing Hdhd in an amount of 3 moles per mole of the $Zr(nBuO)_4$ complex and Hthd in an amount of 1 mole per mole of the $Zr(nBuO)_4$ complex was prepared. To the solution, the mixed solution containing a β diketone compound was slowly added dropwise and the mixture was reacted by heating under reflux at 70° C. for 2 hours. THF in the reaction solution was removed under reduced pressure to obtain a crude product. Then, the resulting crude product was recrystallized in hexane to obtain a purified crystal.

The resulting crystal was identified by elemental analysis. The results of elemental analysis revealed Zr: 12.3% (theoretical value: 12.3%), C: 61.6% (theoretical value: 61.7%) and H: 8.72% (theoretical value: 8.71%). From the results of elemental analysis, the resulting crystal is estimated as a complex in which dhd and thd are coordinated to metallic zirconium and a mixing ratio (dhd/thd) is 75/25 in terms of molar ratio, that is, a complex having a structure of $Zr(dhd)_3(thd)$.

Example 14

In the same manner as in Example 13, except for using, as a mixed solution containing a β diketone compound, a mixed solution containing Hdhd and Hthd in a molar ratio of 50/50, that is, a mixed solution containing Hdhd in an amount of 2 moles per mole of the $Zr(nBuO)_4$ complex and Hthd in an amount of 2 moles per mole of the $Zr(nBuO)_4$ complex, synthesis was conducted to obtain a purified crystal.

The resulting crystal was identified by elemental analysis. The results of elemental analysis revealed Zr: 11.8% (theoretical value: 11.9%), C: 62.6% (theoretical value: 62.5%) and H: 8.92% (theoretical value: 8.92%). From the results of elemental analysis, the resulting crystal is estimated as a complex in which dhd and thd are coordinated to metallic zirconium and a mixing ratio (dhd/thd) is 50/50 in terms of molar ratio, that is, a complex having a structure of $Zr(dhd)_2(thd)_2$.

Example 15

In the same manner as in Example 13, except for using, as a mixed solution containing a β diketone compound, a mixed solution containing Hdhd and Hthd in a molar ratio of 25/75, that is, a mixed solution containing Hdhd in an amount of 1 mole per mole of the $Zr(nBuO)_4$ complex and Hthd in an amount of 3 moles per mole of the $Zr(nBuO)_4$ complex, synthesis was conducted to obtain a purified crystal.

The resulting crystal was identified by elemental analysis. The results of elemental analysis revealed Zr: 11.6% (theoretical value: 11.5%), C: 63.6% (theoretical value: 63.4%) and H: 9.12% (theoretical value: 9.11%). From the results of elemental analysis, the resulting crystal is estimated as a complex in which dhd and thd are coordinated to metallic zirconium and a mixing ratio (dhd/thd) is 25/75 in terms of molar ratio, that is, a complex having a structure of $Zr(dhd)(thd)_3$.

Comparative Example 7

First, a $Zr(nBuO)_4$ complex was used as a starting material of a zirconium material and the starting material was dissolved in toluene as an organic solvent to prepare a 20–27 wt % solution. Then, Hthd was added to the solution in an amount of 4 moles per mole of the $Zr(nBuO)_4$ complex and the mixture was reacted by heating under reflux at 110° C. for 2 hours. Toluene in the reaction solution was removed under reduced pressure to obtain a crude product. Then, the resulting crude product was recrystallized in hexane to obtain a purified crystal made of a $Zr(thd)_4$ complex.

Comparative Example 8

First, a $Zr(tBuO)_4$ complex was used as a starting material of a zirconium material and the starting material was dissolved in toluene as an organic solvent to prepare a 20–27 wt % solution. Then, Hthd was added to the solution in an amount of 2 moles per mole of the $Zr(tBuO)_4$ complex and the mixture was reacted by heating under reflux at 110° C. for 4 hours. Toluene in the reaction solution was removed under reduced pressure to obtain a crude product. Then, the resulting crude product was recrystallized in hexane to obtain a purified crystal made of a $Zr(tBuO)_2(thd)_2$ complex.

Comparative Example 9

In the same manner as in Comparative Example 8, except for replacing the $Zr(tBuO)_4$ complex by a $Zr(tAmylO)_4$ complex, synthesis was conducted to obtain a $Zr(tAmylO)_2(thd)_2$ complex.

Comparative Example 10

First, a $Zr(iPrO)_4$ complex was used as a starting material of a zirconium material and the starting material was dissolved in toluene as an organic solvent to prepare a 20–27 wt % solution. Then, Hthd was added to the solution in an amount of 1 mole per mole of the $Zr(iPrO)_4$ complex and the mixture was reacted by heating under reflux at 110° C. for 4 hours. Toluene in the reaction solution was removed under reduced pressure to obtain a crude product. Then, the resulting crude product was recrystallized in hexane to obtain a purified crystal made of a $Zr_2(iPrO)_6(thd)_2$ complex.

Comparative Example 11

First, a $Zr(iPrO)_4$ complex was used as a starting material of a zirconium material and the starting material was dissolved in toluene as an organic solvent to prepare a 20–27 wt % solution. Then, Hthd was added to the solution in an amount of 3 moles per mole of the $Zr(iPrO)_4$ complex and the mixture was reacted by heating under reflux at 110° C. for 4 hours. Toluene in the reaction solution was removed under reduced pressure to obtain a crude product. Then, the resulting crude product was recrystallized in hexane to obtain a purified crystal made of a $Zr(iPrO)(thd)_3$ complex.

Comparative Example 12

In the same manner as in Comparative Example 10, except for replacing the $Zr(iPrO)_4$ complex by a $Zr(nBuO)_4$ complex, synthesis was conducted to obtain a $Zr(nBuO)(thd)_3$ complex.

Comparative Evaluation 3

Using the zirconium chelate complexes obtained in Examples 13 to 15 and Comparative Example 7, thermogravimetry was conducted under pressure conditions of about 3.99 kPa (30 Torr). The results of thermogravimetry are shown in FIG. 6.

Figure 6:
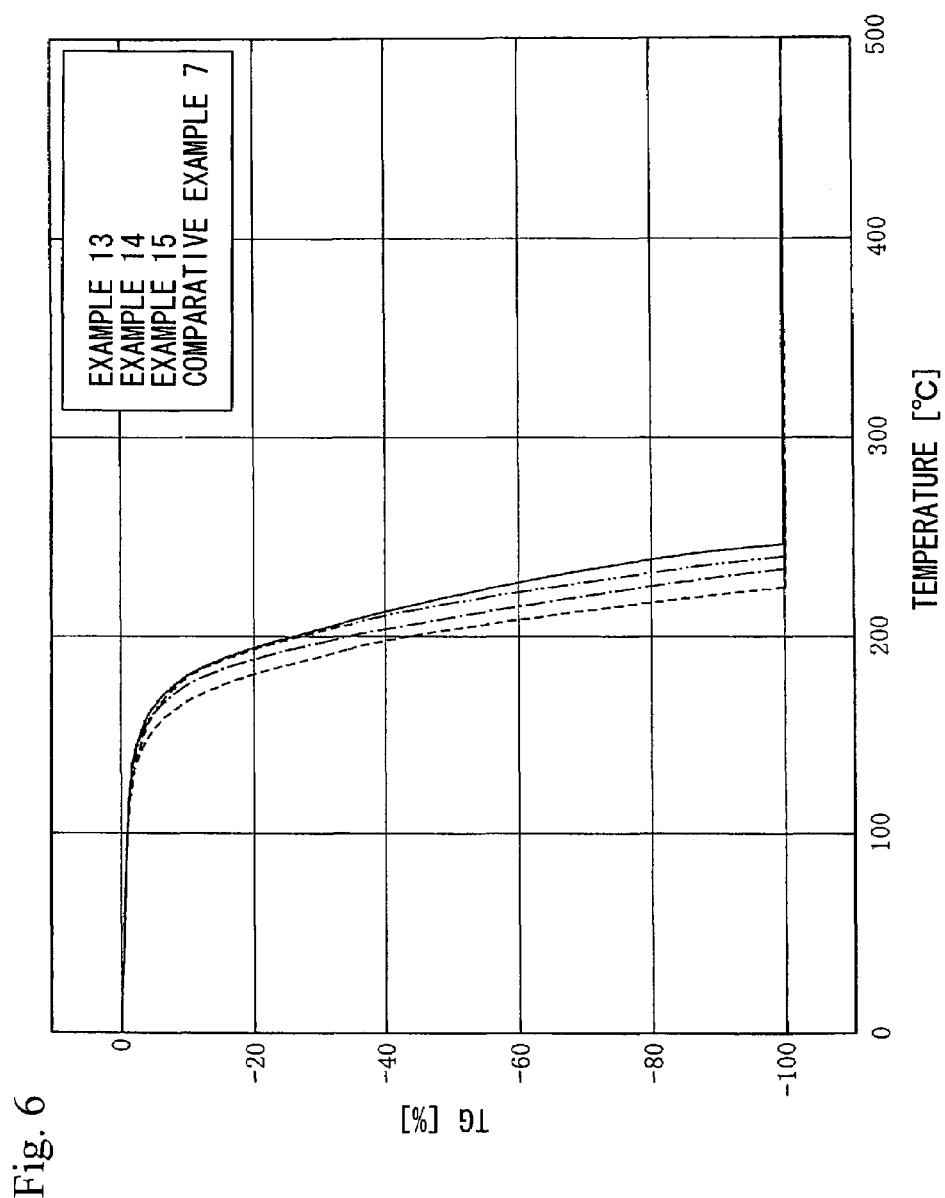
FIG. 6 is a graph showing the results of a TG curve obtained by thermogravimetry of Examples 13 to 15 and Comparative Example 7.

As is apparent from the results of thermogravimetry shown in FIG. 6, the complexes of Examples 13 to 15 exhibited a low vaporization temperature compared to the complex of Comparative Example 7.

Comparative Evaluation 4

The pyrolysis temperature of each of the zirconium chelate complexes obtained in Examples 13 to 15 and Comparative Example 7 was determined. The results are shown in Table 2 below. In Table 2, the pyrolysis temperature of Pb(thd)$_2$ as an organolead compound material of a PZT thin film and that of Ti(iPrO)$_2$(thd)$_2$ as an organotitanium compound material are also shown.

TABLE 2

| | Zirconium chelate complex | Pyrolysis temperature [° C.] |
|---|---|---|
| Example 13 | Zr(dhd)$_3$(thd) | 260 |
| Example 14 | Zr(dhd)$_2$(thd)$_2$ | 280 |
| Example 15 | Zr(dhd)(thd)$_3$ | 300 |
| Comparative Example 7 | Zr(thd)$_4$ | 410 |
| — | Pb(thd)$_2$ | 325 |
| — | Ti(iPrO)$_2$(thd)$_2$ | 280 |

As is apparent from Table 2, the pyrolysis temperature of the complexes of Examples 13 to 15 is lower than that of the complex of Comparative Example 7 and is near the pyrolysis temperature of the organolead compound and the organotitanium compound used to form a PZT dielectric thin film.

Comparative Evaluation 5

First, the zirconium chelate complexes of Examples 13 to 15 and Comparative Examples 8 to 11 were heated to 500° C. in an argon atmosphere and the amount of the vaporization residue was measured by thermogravimetry. Then, the zirconium chelate complexes of Examples 13 to 15 and Comparative Examples 8 to 11 were respectively mixed with a Pb(thd)$_2$ complex in an argon atmosphere and dissolved in THF. These resulting solutions were divided into two portions and each of one portion was stored in an argon atmosphere while being shielded from light for one month, while each of the other portion was stored in the same atmosphere for 3 months. After the completion of the storage, THF was removed under reduced pressure. A mixture obtained by mixing the zirconium chelate complex with the Pb(thd)$_2$ complex was heated to 500° C. in an argon atmosphere and the amount of the vaporization residue was determined by thermogravimetry. The amount of the vaporization residue when using THF as an organic solvent is shown in Table 3.

TABLE 3

| | Zirconium chelate complex | Amount of vaporization residue [% by weight] | | |
|---|---|---|---|---|
| | | Before mixing with Pb(thd)$_2$ | Storage period after mixing | |
| | | | 1 month | 3 months |
| Example 13 | Zr(dhd)$_3$(thd) | 0.9 | 1.1 | 1.0 |
| Example 14 | Zr(dhd)$_2$(thd)$_2$ | 0.8 | 1.0 | 0.8 |
| Example 15 | Zr(dhd)(thd)$_3$ | 0.7 | 1.0 | 0.9 |
| Comparative Example 8 | Zr(tBuO)$_2$(thd)$_2$ | 7.5 | 13.4 | 16.2 |
| Comparative Example 9 | Zr(tAmylO)$_2$(thd)$_2$ | 7.2 | 9.8 | 11.6 |
| Comparative Example 10 | Zr$_2$(iPrO)$_6$(thd)$_2$ | 6.8 | 11.8 | 14.5 |
| Comparative Example 11 | Zr(iPrO)(thd)$_3$ | 9.5 | 10.1 | 11.5 |

As is apparent from Table 3, with respect to the results of thermogravimetry in the case of the zirconium chelate complex alone before mixing with Pb(thd)$_2$, 6.8 to 9.5% by weight of the vaporization residue remained in the zirconium chelate complexes of Comparative Examples 8 to 11, while a small amount (0.7 to 0.9% by weight) of the vaporization residue remained in the zirconium chelate complexes of Examples 13 to 15. In the case in which the zirconium chelate complex was mixed with Pb(thd)$_2$ and the mixture was stored for one month, 9.8 to 13.4% by weight of the vaporization residue remained in the zirconium chelate complexes of Comparative Examples 8 to 11, while a small amount (1.0 to 1.1% by weight) of the vaporization residue remained in the zirconium chelate complexes of Examples 13 to 15. In the case in which the mixture was stored for 3 months, 11.5 to 16.2% by weight of the vaporization residue remained in the zirconium chelate complexes of Comparative Examples 8 to 11, while a small amount (0.8 to 1.0% by weight) of the vaporization residue remained in the zirconium chelate complexes of Comparative Examples 13 to 15.

Comparative Evaluation 6

First, the zirconium chelate complexes of Examples 13 to 15 and Comparative Examples 8 to 11 were heated to 500° C. in an argon atmosphere and the amount of the vaporization residue was measured by thermogravimetry. Then, the zirconium chelate complexes of Examples 13 to 15 and Comparative Examples 8 to 11 were respectively mixed with a Pb(thd)$_2$ complex in an argon atmosphere and dissolved in CyHex. These resulting solutions were divided into two portions and each of one portion was stored in an argon atmosphere while being shielded from light for one month, while each of the other portion was stored in the same atmosphere for 3 months. After the completion of the storage, CyHex was removed under reduced pressure. A mixture obtained by mixing the zirconium chelate complex with the Pb(thd)$_2$ complex was heated to 500° C. in an argon atmosphere and the amount of the vaporization residue was determined by thermogravimetry. The amount of the vaporization residue when using CyHex as an organic solvent is shown in Table 4.

TABLE 4

| | | Amount of vaporization residue [% by weight] | | |
|---|---|---|---|---|
| | Zirconium chelate | Before mixing with | Storage period after mixing | |
| | complex | Pb(thd)$_2$ | 1 month | 3 months |
| Example 13 | Zr(dhd)$_3$(thd) | 0.9 | 1.0 | 1.0 |
| Example 14 | Zr(dhd)$_2$(thd)$_2$ | 0.8 | 0.8 | 0.9 |
| Example 15 | Zr(dhd)(thd)$_3$ | 0.7 | 0.9 | 0.9 |
| Comparative Example 8 | Zr(tBuO)$_2$(thd)$_2$ | 7.2 | 15.2 | 18.3 |
| Comparative Example 9 | Zr(tAmylO)$_2$(thd)$_2$ | 7.9 | 10.8 | 12.9 |
| Comparative Example 10 | Zr$_2$(iPrO)$_6$(thd)$_2$ | 7.4 | 12.3 | 15.4 |
| Comparative Example 11 | Zr(iPrO)(thd)$_3$ | 9.3 | 13.2 | 13.8 |

As is apparent from Table 4, with respect to the results of thermogravimetry in the case of the zirconium chelate complex alone before mixing with Pb(thd)$_2$, 7.2 to 9.3% by weight of the vaporization residue remained in the zirconium chelate complexes of Comparative Examples 8 to 11, while a small amount (0.7 to 0.9% by weight) of the vaporization residue remained in the zirconium chelate complexes of Examples 13 to 1 5. In the case in which the zirconium chelate complex is mixed with Pb(thd)$_2$ and the mixture was stored for one month, 10.8 to 15.2% by weight of the vaporization residue remained in the zirconium chelate complexes of Comparative Examples 8 to 11, while a small amount (0.8 to 1.0% by weight) of the vaporization residue remained in the zirconium chelate complexes of Examples 13 to 15. In the case in which the mixture was stored for 3 months, 12.9 to 18.3% by weight of the vaporization residue remained in the zirconium chelate complexes of Comparative Examples 8 to 11, while a small amount (0.9 to 1.0% by weight) of the vaporization residue remained in the zirconium chelate complexes of Comparative Examples 13 to 15.

Comparative Evaluation 7

Using the zirconium chelate complexes of Examples 13 to 15 and Comparative Examples 11 to 12, each of the zirconium chelate complexes was mixed with other metal chelate complexes, with the composition shown in FIG. 6, and the mixture was dissolved in an organic solvent to prepare a raw material solution.

Using a vaporizer, which is commercially available as a vaporizer for MOCVD apparatus, the resulting raw material solution was vaporized under the conditions shown in Table 5 below. The vaporization results are shown in Table 6. After recovering the vaporization residue, a residue ratio in Table 6 was determined by calculating based on the following equation.

Residue ratio=(amount of vaporization residue/weight of compound before dissolution)×100 (%)

TABLE 5

| Vaporization temperature | Vaporization pressure | Flow rate of raw material | Flow rate of N$_2$ | Test time |
|---|---|---|---|---|
| 250° C. | 4000 Pa | 0.2 cc/min | 200 sccm | 80 hours |

TABLE 6

| | Zr chelate complex | Pb chelate complex | Ti chelate complex | Organic solvent | Residue ratio [%] |
|---|---|---|---|---|---|
| Example 13 | Zr(dhd)$_3$(thd) | Pb(thd)$_2$ | — | THF | 0.1 |
| | Zr(dhd)$_3$(thd) | Pb(thd)$_2$ | Ti(iPrO)$_2$(thd)$_2$ | THF | 0.2 |
| | Zr(dhd)$_3$(thd) | Pb(thd)$_2$ | — | CyHex | 0.1 |
| | Zr(dhd)$_3$(thd) | Pb(thd)$_2$ | Ti(iPrO)$_2$(thd)$_2$ | CyHex | 0.2 |
| Example 14 | Zr(dhd)$_2$(thd)$_2$ | Pb(thd)$_2$ | — | THF | 0.1 |
| | Zr(dhd)$_2$(thd)$_2$ | Pb(thd)$_2$ | Ti(iPrO)$_2$(thd)$_2$ | THF | 0.2 |
| | Zr(dhd)$_2$(thd)$_2$ | Pb(thd)$_2$ | — | CyHex | 0.1 |
| | Zr(dhd)$_2$(thd)$_3$ | Pb(thd)$_2$ | Ti(iPrO)$_2$(thd)$_2$ | CyHex | 0.2 |
| Example 15 | Zr(dhd)(thd)$_3$ | Pb(thd)$_2$ | — | THF | 0.1 |
| | Zr(dhd)(thd)$_3$ | Pb(thd)$_2$ | Ti(iPrO)$_2$(thd)$_2$ | THF | 0.2 |
| | Zr(dhd)(thd)$_3$ | Pb(thd)$_2$ | — | CyHex | 0.1 |
| | Zr(dhd)(thd)$_3$ | Pb(thd)$_2$ | Ti(iPrO)$_2$(thd)$_2$ | CyHex | 0.2 |
| Comparative Example 11 | Zr(iPrO)(thd)$_3$ | Pb(thd)$_2$ | — | THF | 2.0 |
| | Zr(iPrO)(thd)$_3$ | Pb(thd)$_2$ | Ti(iPrO)$_2$(thd)$_2$ | THF | 6.3 |

TABLE 6-continued

| | Zr chelate complex | Pb chelate complex | Ti chelate complex | Organic solvent | Residue ratio [%] |
|---|---|---|---|---|---|
| Comparative Example 12 | Zr(nBuO)(thd)$_3$ | Pb(thd)$_2$ | Ti(iPrO)$_2$(thd)$_2$ | THF | 7.1 |

As is apparent from Table 6, the residue ratio of the raw material solutions using the zirconium chelate complexes of Comparative Examples 11 and 12 was large (2.0 to 7.1%), and therefore it is impossible to say that a film can be stably formed. On the other hand, the residue ratio of the raw material solutions using the zirconium chelate complexes of Examples 13 to 15 was 0.1 to 0.2%. Consequently, the residue ratio can be reduced to a minimum and a film can be stably formed by using the raw material solution containing the zirconium chelate complex of the present invention, and thus the composition of a PZT thin film can be precisely controlled over a broad temperature range.

Example 16

Zr(thd)$_4$ was prepared as a first zirconium chelate complex $C_1$ and Zr(dhd)$_4$ was prepared as a second zirconium chelate complex $C_2$, respectively. The first zirconium chelate complex and the second zirconium chelate complex were mixed in THF in a mixing ratio ($C_1/C_2$) of 50/50 in terms of molar ratio to prepare a raw material solution.

Example 17

In the same manner as in Example 16, except for preparing in a mixing ratio ($C_1/C_2$) of 80/20 in terms of molar ratio, a raw material solution was obtained.

Comparative Example 13

Zr(thd)$_4$ as a zirconium chelate complex was dissolved in THF to prepare a raw material solution.

Comparative Example 14

Zr(dhd)$_4$ as a zirconium chelate complex was dissolved in THF to prepare a raw material solution.

Comparative Evaluation 8

Figure 7:
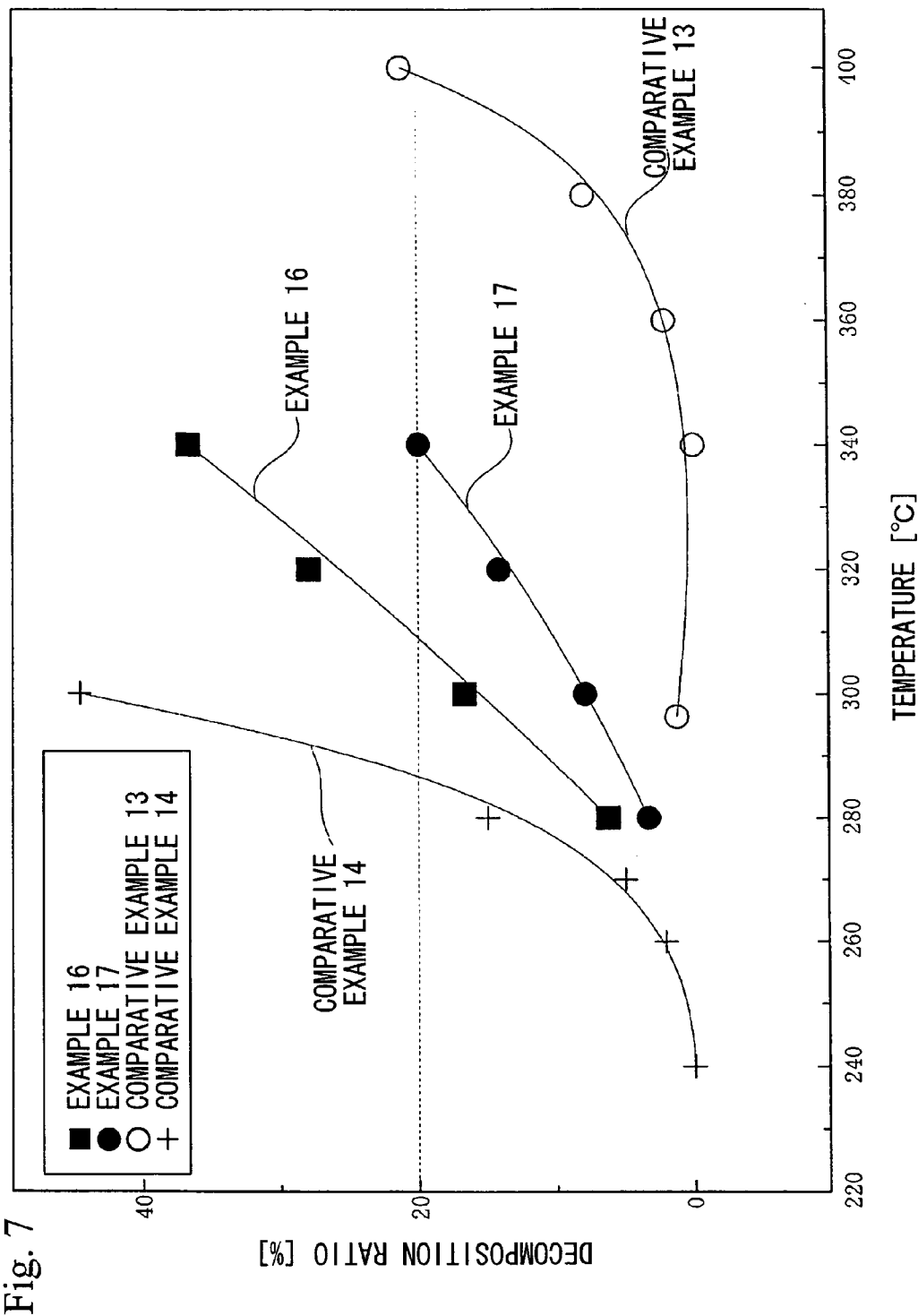
FIG. 7 is a graph showing relationships between the heating temperature and the decomposition ratio in Examples 16 and 17 and Comparative Examples 13 and 14.
Figure 8:
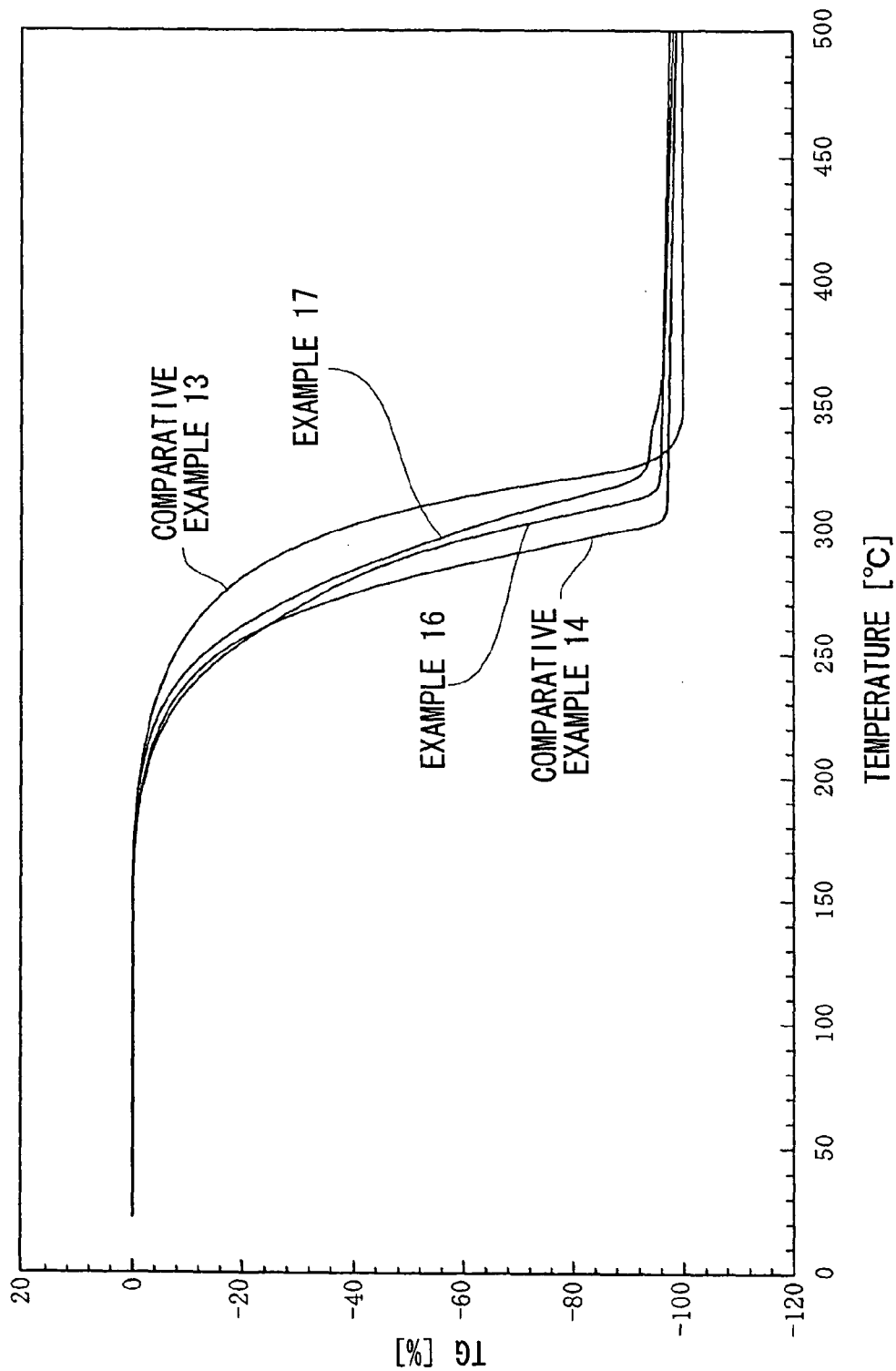
FIG. 8 is a graph showing the results of a TG curve obtained by thermogravimetry of Examples 16 and 17 and Comparative Examples 13 and 14.

The raw material solutions of Examples 16 and 17 and Comparative Examples 13 and 14 and, after 24 hours, the raw material solutions were allowed to stand under reduced pressure, thereby to vaporize THF to obtain zirconium chelate complexes. The resulting zirconium chelate complexes of Examples 16 and 17 and Comparative Examples 13 and 14 were heated to an arbitrary temperature and the decomposition ratio was measured. The results are shown in FIG. 7. In FIG. 7, the temperature, at which the decomposition ratio exceeds 20% after heating to arbitrary temperature for one hour, was defined as a decomposition temperature. The zirconium chelate complexes of Examples 16 and 17 and Comparative Examples 13 to 14 were subjected to thermogravimetry while heating at a heating rate of 10° C./min. The results are shown in FIG. 8.

As is apparent from FIG. 7, the decomposition temperatures of the zirconium chelate complexes of Examples 16 and 17 are within the range of the decomposition temperatures of Zr(dhd)$_4$ and Zr(thd)$_4$ of Comparative Examples 13 and 14. It is also apparent that the decomposition temperature can be controlled by the mixing ratio of Zr(dhd)$_4$ and Zr(thd)$_4$. Consequently, it is made possible to control to the decomposition temperature which is near the decomposition temperatures of Pb(dhd)$_2$, Ti(iPrO)$_2$(thd)$_2$ and Ti(tBuO)$_2$(thd)$_2$ as the PZT thin film material. As is apparent from FIG. 8, the vaporization temperatures of the zirconium chelate complexes of Examples 16 and 17 are within the range of the vaporization temperatures of Zr(dhd)$_4$ and Zr(thd)$_4$ of Comparative Examples 13 and 14 and the vaporization temperature can be controlled by the mixing ratio of Zr(dhd)$_4$ and Zr(thd)$_4$.

Example 18

Zr(dhd)$_4$ and Zr(thd)$_4$, as the zirconium chelate complex, were mixed in an equimolar ratio and the mixture was divided into four portions. Two portions were further mixed with Pb(dtd)$_2$ in an inert atmosphere and then respectively dissolved in THF and CyHex to prepare raw material solutions. The remaining two portions were respectively dissolved in THF and CyHex without being mixed with Pb(thd)$_2$ to prepare raw material solutions.

Comparative Example 15

In the same manner as in Example 18, except for using Zr(tBuO)$_2$(thd)$_2$ as a zirconium chelate complex, a raw material solution was prepared.

Comparative Example 16

In the same manner as in Example 18, except for using Zr(tAmylO)$_2$(thd)$_2$ as a zirconium chelate complex, a raw material solution was prepared.

Comparative Example 17

In the same manner as in Example 18, except for using Zr$_2$(iPrO)$_6$(thd)$_2$ as a zirconium chelate complex, a raw material solution was prepared.

Comparative Example 18

In the same manner as in Example 18, except for using Zr(iPrO)(thd)$_3$ as a zirconium chelate complex, a raw material solution was prepared.

Comparative Evaluation 9

The raw material solutions of Example 18 and Comparative Examples 15 to 18 were stored in an inert atmosphere while being shielded from light for one month. After the completion of storing, the respective solvents were removed under reduced pressure and the zirconium chelate complexes were subjected to thermogravimetry. Changes in vaporization residue ratio before and after mixing with Pb(thd)$_2$ are shown in Table 7.

TABLE 7

| Zirconium chelate complex | Organic solvent | Vaporization residue [% by weight] | |
|---|---|---|---|
| | | Before mixing | After mixing |
| Example 18 Zr(dhd)$_4$:Zr(thd)$_4$ = 1:1 | THF | 1.5 | 2.1 |
| | CyHex | 1.5 | 2.4 |
| Comparative Example 15 Zr(tBuO)$_2$(thd)$_2$ | THF | 7.5 | 26.2 |
| | CyHex | 7.5 | 27.6 |
| Comparative Example 16 Zr(tAmylO)$_2$(thd)$_2$ | THF | 7.2 | 21.5 |
| | CyHex | 7.2 | 22.4 |
| Comparative Example 17 Zr$_2$(iPrO)$_6$(thd)$_2$ | THF | 6.8 | 31.5 |
| | CyHex | 6.8 | 32.3 |
| Comparative Example 18 Zr(iPrO)(thd)$_3$ | THF | 9.5 | 15.5 |
| | CyHex | 9.5 | 16.7 |

As is apparent from Table 7, with respect to the results of thermogravimetry in the case of the zirconium chelate complex alone before mixing with Pb(thd)$_2$, 6.8 to 9.5% by weight of the vaporization residue remained in the zirconium chelate complexes of Comparative Examples 15 to 18, while a small amount (1.5% by weight) of the vaporization residue remained in the zirconium chelate complex of Example 18. In the case in which the zirconium chelate complex was mixed with Pb(thd)$_2$ and the mixture was stored for one month, 15.5 to 32.3% by weight of the vaporization residue remained in the zirconium chelate complexes of Comparative Examples 15 to 18, while a small amount (2.1 to 2.4% by weight) of the vaporization residue remained in the zirconium chelate complex of Example 18. The reason is believed to be as follows. That is, in the case of the zirconium chelate complex of Example 18 in which four β diketone compounds coordinate to metallic zirconium, all eight coordination sites of zirconium are occupied and high stability can be maintained, while in the cases of the zirconium chelate complexes containing an alkoxide such as Zr$_2$(iPrO)$_6$(thd)$_2$ or Zr(iPrO)(thd)$_3$ of Comparative Examples 17 and 18, merely six or seven coordination sites in all coordination sites of zirconium are occupied and all coordination sites cannot be occupied; therefore, the stability is degraded compared to the compound in which all coordination sites are occupied, and thus the complexes react with surrounding Pb(thd)$_2$ to form a vaporization residue in a large amount. Also it is believed that Pb alkoxide was formed. The amount of the vaporization residue slightly varied depending on the kind of the organic solvent.

Comparative Evaluation 10

THF raw material solutions of Example 16 and Comparative Examples 13 and 14, each having a concentration of 0.3 moles, were prepared and a PZT dielectric thin film was formed on a substrate at different film forming temperatures using a film forming apparatus shown in FIG. 9. The film forming conditions are shown in Table 8 below. The film forming results of the resulting thin films are shown in FIG. 10.

TABLE 8

| | | | |
|---|---|---|---|
| Film forming temperature | 420 to 620° C. | Organolead compound | Pb(thd)$_2$ |
| Film forming time | 150 to 200 sec | Organotitanium compound | Ti(iPrO)$_2$(thd)$_2$ |
| Reaction pressure | 532 Pa (4 Torr) | Flow rate of lead solution | 0.40 ml/min |
| Vaporization temperature | 210° C. | Flow rate of Zr solution | 0.35 ml/min |
| Flow rate of oxygen gas | 2.5 slm | Flow rate of titanium solution | 0.12 ml/min |
| Flow rate of He gas (Carrier gas) | 250 sccm | Substrate | PbTiO$_3$/Pt/SiO$_2$/Si (5 nm/200 nm/500 nm) |
| Concentration of raw material solution | 0.3 mol/l | | |

Figure 10:
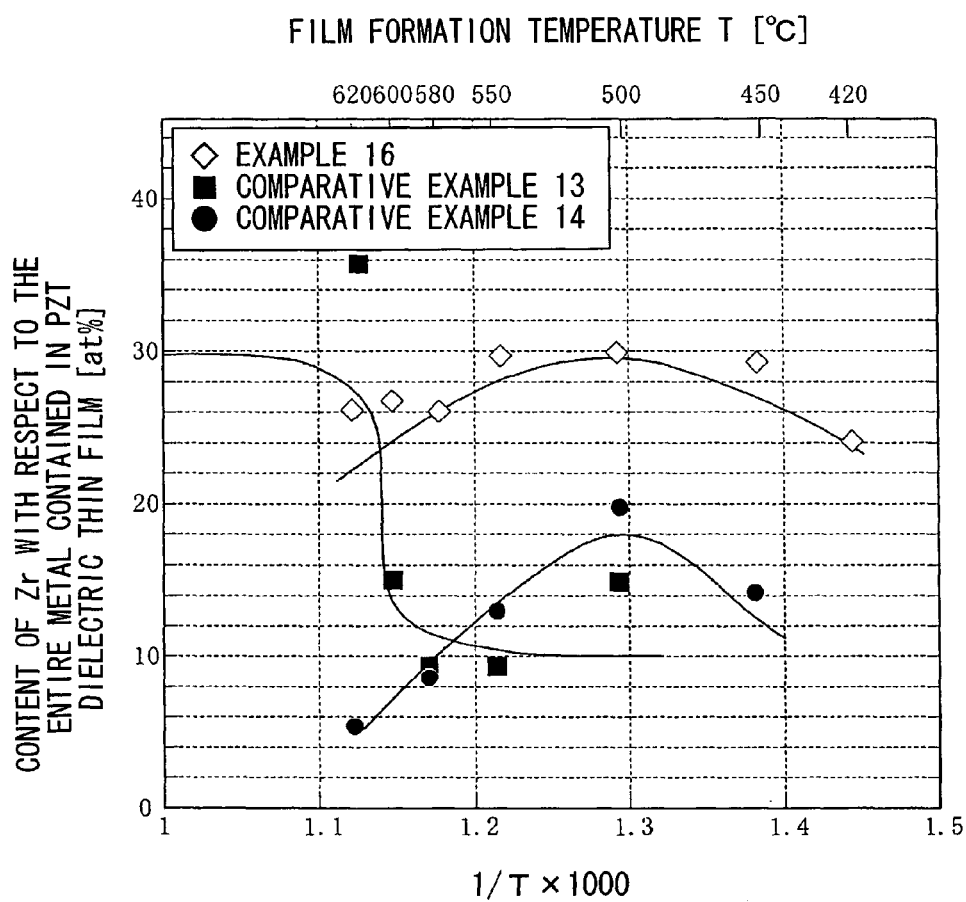
FIG. 10 is a graph showing relationships between the film forming temperature and the Zr content in a PZT dielectric thin film in a raw material solution of Example 18 and Comparative Examples 13 and 14.

As is apparent from FIG. 10. in the PZT dielectric thin films formed by using the raw material solutions of Comparative Examples 13 and 14, the mixing ratio of zirconium with the entire metal contained in the thin film was small at any film forming temperature and, consequently, it is impossible to say that the feed flow rate of the zirconium material was sufficient. On the other hand, in the PZT dielectric thin film formed by using the raw material solution of Example 16, the mixing ratio of zirconium with the entire metal is about 30% any film forming temperature and, consequently, it has been found that the composition of the PZT dielectric thin film can be precisely controlled over a broad temperature range by using the organozirconium composite of the present invention.

As described above, the organozirconium composite of the present invention comprises one, or at least two kinds of zirconium chelate complexes containing, as a ligand, both of a first β diketone and a second β diketone having a structure different from that of the first β diketone, in which when at least two kinds of zirconium chelate complexes are contained, the coordination numbers of the first β diketone and the second β diketone that coordinates to at least two kinds of zirconium chelate complexes vary depending on the respective zirconium chelate complexes. Such an organozirconium composite has a decomposition temperature which is near the respective decomposition temperatures of an organolead compound and an organotitanium compound. Therefore, when a film is formed by the MOCVD method using the complex as a material, the composition of a PZT thin film can be more precisely controlled over a broad temperature range. The raw material solution of the present invention is less likely to react with an organolead compound when mixed with the organolead compound. Therefore, the raw material solution is also useful as a raw material solution which further contains an organolead compound and an organotitanium compound. Also the raw material solution is less likely to cause vapor phase cracking.

What is claimed is:

1. An organozirconium composite comprising one, or at least two kinds of zirconium chelate complexes comprising, as a ligand, both of a first β diketone and a second β diketone having a structure different from that of the first β diketone, wherein when the organozirconium composite comprises at least two kinds of zirconium chelate complexes, the coordination numbers of the first β diketone and the second β diketone that coordinate to at least two kinds of zirconium chelate complexes vary depending on the respective zirconium chelate complexes.

2. The organozirconium composite according to claim 1, further comprising at least one of a first β diketone ligand and a second β diketone ligand.

3. The organozirconium composite according to claim 1, further comprising at least one of a zirconium chelate complex containing only the first β diketone as a ligand and a zirconium chelate complex containing only the second β diketone as a ligand.

4. The organozirconium composite according to claim 1, wherein the first β diketone and the second β diketone are compounds selected from the group consisting of 2,2,6,6-tetramethyl-3,5-heptanedione residue, 2,6-dimethyl-3,5-heptanedione residue, acetylacetone residue, hexafluoroacetylacetone residue, trifluoroacetylacetone residue, trimethyloctanedione residue and diphenylpropanedione residue.

5. The organozirconium composite according to claim 1, wherein the zirconium chelate complex is obtained by reacting at least two kinds of β diketone compounds with a zirconium compound.

6. The organozirconium composite according to claim 5, wherein the zirconium chelate complex is a complex obtained by reacting at least two kinds of β diketone compounds with a zirconium compound, wherein a mixing ratio of two kinds of β diketone compounds, that is, a mixing ratio of one β diketone compound A with the other β diketone compound B, (A/B), is from 80/20 to 20/80 in terms of molar ratio.

7. The organozirconium composite according to claim 5, wherein at least two kinds of β diketone compounds are compounds selected from the group consisting of 2,6-dimethyl-3,5-heptanedione, 2,2,6,6-tetramethyl-3,5-heptanedione, acetylacetone, hexafluoroacetylacetone, trifluoroacetylacetone, trimethyloctanedione and diphenylpropanedione.

8. The organozirconium composite according to claim 5, wherein one β diketone compound is 2,6-dimethyl-3,5-heptanedione and the other β diketone compound is 2,2,6,6-tetramethyl-3,5-heptanedione.

9. A method of synthesizing an organozirconium composite, which comprises mixing a first β diketone compound with a zirconium chelate complex containing, as a ligand, a second β diketone having a structure different from that of the first β diketone compound.

10. The method of synthesizing an organozirconium composite according to claim 9, wherein the amount of the first β diketone compound is within a range from 100 to 1600 mol % based on the zirconium chelate complex containing the second β diketone as a ligand.

11. The method of synthesizing an organozirconium composite according to claim 9, wherein the first β diketone compound is 2,2,6,6-tetramethyl-3,5-heptanedione and the zirconium chelate complex containing the second β diketone as a ligand is tetrakis-2,6-dimethyl-3,5-heptanedionate zirconium.

12. The method of synthesizing an organozirconium composite according to claim 9, wherein the first β diketone compound is 2,6-dimethyl-3,5-heptanedione and the zirconium chelate complex containing the second β diketone as a ligand is tetrakis-2,2,6,6-tetramethyl-3,5-heptanedionate zirconium.

13. A method of synthesizing an organozirconium composite, which comprises dissolving a zirconium compound selected from zirconium butoxide, zirconium chloride and zirconium chloride oxide in an organic solvent, adding a mixed solution containing at least two kinds of β diketone compounds to the resulting solution, and heating the mixed solution under reflux at a temperature higher than a boiling point of the organic solvent contained in the mixed solution.

14. The method of synthesizing an organozirconium composite according to claim 13, comprising reacting two kinds of β diketone compounds with a zirconium compound, wherein a mixing ratio of two kinds of β diketone compounds, that is, a mixing ratio of one β diketone compound A with the other β diketone compound B, (A/B), is from 80/20 to 20/80 in terms of molar ratio.

15. The method of synthesizing an organozirconium composite according to claim 13, wherein at least two kinds of β diketone compounds are compounds selected from the group consisting of 2,6-dimethyl-3,5-heptanedione, 2,2,6,6-tetramethyl-3,5-heptanedione, acetylacetone, hexafluoroacetylacetone, trifluoroacetylacetone, trimethyloctanedione and diphenylpropanedione.

16. The method of synthesizing an organozirconium composite according to claim 13, wherein one β diketone compound is 2,6-dimethyl-3,5-heptanedione and the other β diketone compound is 2,2,6,6-tetramethyl-3,5-heptanedione.

17. A raw material solution comprising an organic solvent and the organozirconium composite of claim 1 dissolved in the organic solvent.

18. A raw material solution comprising an organic solvent and an organozirconium composite obtained by the synthesis method of claim 9 dissolved in the organic solvent.

19. A raw material solution containing an organozirconium composite, comprising an organic solvent, and a first zirconium chelate complex in which a single kind of a β diketone compound is coordinated to a center metal and a second zirconium chelate complex in which a single kind of a β diketone compound different from the β diketone compound is coordinated to a center metal, which are dissolved in an organic solvent.

20. The raw material solution according to claim 19, wherein a mixing ratio of first and second zirconium chelate complexes, that is, a mixing ratio of a first zirconium chelate complex $C_1$ with a second zirconium chelate complex $C_2$, $(C_1/C_2)$, is from 10/90 to 90/10 in terms of molar ratio.

21. The raw material solution according to claim 19, wherein the first and second zirconium chelate complexes are complexes selected from the group consisting of tetrakis-2,6-dimethyl-3,5-heptanedionate zirconium, tetrakis-2,2,6,6-tetramethyl-3,5-heptanedionate zirconium, tetrakisacetylacetonate zirconium, tetrakishexafluoroacetylacetonate zirconium, tetrakistrifluoroacetylacetonate zirconium, tetrakistrimethyloctanedionate zirconium and tetrakisdiphenylpropanedionate zirconium.

22. The raw material solution according to claim 19, wherein the first zirconium chelate complex is tetrakis-2,2,6,6-tetramethyl-3,5-heptanedionate zirconium and the second zirconium chelate complex is tetrakis-2,6-dimethyl-3,5-heptanedionate zirconium.

23. The raw material solution according to claim 17, wherein the organic solvent comprises one, or at least two kinds of solvents selected from the group consisting of tetrahydrofuran, methyltetrahydrofuran, n-octane, iso-octane, hexane, cyclohexane, pyridine, lutidine, butyl acetate and amyl acetate.

24. The raw material solution according to claim 18, wherein the organic solvent comprises one, or at least two kinds of solvents selected from the group consisting of tetrahydrofuran, methyltetrahydrofuran, n-octane, iso-octane, hexane, cyclohexane, pyridine, lutidine, butyl acetate and amyl acetate.

25. The raw material solution according to claim 19, wherein the organic solvent comprises one, or at least two kinds of solvents selected from the group consisting of tetrahydrofuran, methyltetrahydrofuran, n-octane, iso-octane, hexane, cyclohexane, pyridine, lutidine, butyl acetate and amyl acetate.

26. The raw material solution according to claim 17, further comprising at least one of an organolead compound and an organotitanium compound.

27. The raw material solution according to claim 18, further comprising at least one of an organolead compound and an organotitanium compound.

28. The raw material solution according to claim 19, further comprising at least one of an organolead compound and an organotitanium compound.

29. A method of making a lead zirconate titanate thin film comprising forming the thin film by metal organic chemical vapor deposition of the organozirconium composite of claim 1 onto a heated substrate, wherein the composite is thermally decomposed prior to being deposited onto the substrate.

30. A method of making a lead zirconate titanate thin film comprising forming the thin film by metal organic chemical vapor deposition of the organozirconium composite obtained by the method of claim 9 onto a heated substrate, wherein the composite is thermally decomposed prior to being deposited on the substrate.

31. A method of making a lead zirconate titanate thin film comprising forming the thin film by metal organic chemical vapor deposition of the organozirconium composite obtained by the method of claim 13 onto a heated substrate, wherein the composite is thermally decomposed prior to being deposited on the substrate.

32. A method of making a lead zirconate titanate thin film comprising forming the thin film by metal organic chemical vapor deposition of the raw material solution of claim 17 onto a heated substrate, wherein the solution is thermally decomposed prior to being deposited on the substrate.

33. A method of forming a lead zirconate titanate thin film comprising forming the thin film by metal organic chemical vapor deposition of the raw material solution of claim 18 onto a heated substrate, wherein the solution is thermally decomposed prior to being deposited on the substrate.

34. A method of making a lead zirconate titanate thin film comprising forming the thin film by metal organic chemical vapor deposition of the raw material solution of claim 19 onto a heated substrate, wherein the solution is thermally decomposed prior to being deposited on the substrate.

* * * * *